(12) United States Patent
Aigner et al.

(10) Patent No.: US 10,984,892 B2
(45) Date of Patent: Apr. 20, 2021

(54) METHODS OF EVALUATING MEDICAL MEASUREMENT CURVES, AS WELL AS COMPUTER PROGRAMS AND DEVICES THEREFOR

(71) Applicant: Roche Diabetes Care, Inc., Indianapolis, IN (US)

(72) Inventors: Simon Aigner, Heidelberg (DE); Gabriele Chemnitius, Mannheim (DE); Carina Horn, Biblis (DE); Bernd Limburg, Soergenloch (DE); Timo Ottenstein, Heidelberg (DE); Wolfgang Petrich, Bad Schoenborn (DE); Markus Plum, Mainz (DE); Christian Ringemann, Mannheim (DE); Markus Serr, Zug (CH)

( * ) Notice: Subject to any disclaimer, the term of this patent is extended or adjusted under 35 U.S.C. 154(b) by 0 days.

(21) Appl. No.: 16/502,363

(22) Filed: Jul. 3, 2019

(65) Prior Publication Data

US 2019/0325992 A1 Oct. 24, 2019

Related U.S. Application Data

(63) Continuation of application No. 14/744,971, filed on Jun. 19, 2015, now abandoned, which is a continuation of application No. PCT/EP2013/077348, filed on Dec. 19, 2013.

(30) Foreign Application Priority Data

Dec. 20, 2012 (EP) ..................................... 12198445

(51) Int. Cl.
| | |
|---|---|
| *G16B 40/00* | (2019.01) |
| *G01N 21/27* | (2006.01) |
| *G01N 21/84* | (2006.01) |
| *G01N 21/77* | (2006.01) |
| *G01N 33/66* | (2006.01) |
| *G01N 33/80* | (2006.01) |

(52) U.S. Cl.
CPC ........... *G16B 40/00* (2019.02); *G01N 21/274* (2013.01); *G01N 21/77* (2013.01); *G01N 21/8483* (2013.01); *G01N 33/66* (2013.01); *G01N 33/80* (2013.01); *G01N 2201/129* (2013.01); *Y10T 436/144444* (2015.01)

(58) Field of Classification Search
CPC ........... G01N 33/54313; G01N 33/543; G01N 33/53; G01N 33/50
USPC .......................................................... 436/70
See application file for complete search history.

(56) References Cited

U.S. PATENT DOCUMENTS 5,420,042 A 5/1995 Schafer

FOREIGN PATENT DOCUMENTS

| WO | 2004099763 A1 | 11/2004 |
|---|---|---|
| WO | 2006138226 A2 | 12/2006 |
| WO | 2009099269 A1 | 8/2009 |
| WO | 2011131490 A2 | 10/2011 |
| WO | 2012054532 A1 | 4/2012 |

OTHER PUBLICATIONS

Written Opinion of the ISR for PCT/EP2013/077348, dated Jan. 22, 2016, Published on Jun. 2015, pp. 1-7.

*Primary Examiner* — Christine T Mui
(74) *Attorney, Agent, or Firm* — Quarles & Brady LLP

(57) ABSTRACT

Methods are provided for detecting an analyte concentration/presence in a body fluid sample that include providing a set of at least two different evaluation rules, each evaluation rule adapted to derive a set characteristic values from an optical measurement curve, where at least one first characteristic value is derived from at least one first evaluation rule and at least one second characteristic value is derived from at least one second evaluation rule. The methods also include performing at least one multivariate analysis of the at least one first and second characteristic values by using at least one predetermined multivariate evaluation algorithm to derive at least one estimate value for at least one target variable Y of the state variables. The methods also include determining at least one analyte concentration by using the at least one target variable Y. Also provided are computer programs and devices that incorporate the same.

20 Claims, 10 Drawing Sheets

METHODS OF EVALUATING MEDICAL MEASUREMENT CURVES, AS WELL AS COMPUTER PROGRAMS AND DEVICES THEREFOR

CROSS-REFERENCE TO RELATED APPLICATIONS

This patent application is a continuation of U.S. application Ser. No. 14/744,971 filed Jun. 16, 2015, which is a continuation of PCT/EP2013/077348 filed Dec. 19, 2013, which claims benefit of European Patent Application 12198445.4 filed Dec. 20, 2012. Each patent application is incorporated herein by reference as set forth in its entirety.

TECHNICAL FIELD

This patent application relates generally to medicine/medical diagnostics and mathematics, and more particularly, it relates to methods of detecting an analyte concentration in a body fluid sample, and methods of characterizing a body fluid sample, as well a computer programs and devices that incorporate the same.

BACKGROUND

In the field of medical diagnostics, in many cases, one or more analytes have to be detected in body fluid samples such as, for example, blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

In known devices and methods such as, for example, in analytical test systems, a time evolution of a measurement signal is observed after inserting or positioning the sample in or on the test system. Usually, such devices and methods use test elements having one or more test chemistries, which, in presence of the analyte to be detected, are capable of performing one or more detectable detection reactions such as, for example, optically detectable detection reactions.

von Ketteler et al. discloses that spectroscopic properties of highly purified cNADH could be determined for the first time and were compared to those of NADH. See, von Ketteler et al. (2012) *Chemphyschem.* 13:1302-1306. Carbanicotinamide adenine dinucleotide (cNAD) may serve as a stable co-factor for an enzyme-based detection of glucose. When changing from NADH to cNADH, an about 50% increase in quantum efficiency could be observed, which—together with a large excitation wavelength and a higher stability—should make cNAD a well suited alternative as coenzyme for robust glucose detection.

EP Patent Application Publication No. 2 006 786 discloses a method and a glucose monitoring system for monitoring individual metabolic response and for generating nutritional feedback. The method includes a step of consecutively performing a plurality of measurements of a glucose level in a qualified subject by a measuring device. In the measuring device, first data corresponding to a measured glucose level is generated. This data is further transmitted to an analysis device. There, second data is generated representing at least one measure for variability of a glucose level of the subject from a time-series of glucose measurement represented by the first data. Embodiments are explained by presenting phase space diagrams (e.g., by a phase space diagram representing the glucose value) as well as the first derivative of the glucose progressions. Suitable frequencies for taking measurements are from 4 (i.e., a measurement every 15 minutes) to 60 (i.e., a measurement every minute) measurements an hour.

A representation of a function with their first derivative is well known in physics such as, for example, in presentations of space and momentum. See, e.g., Gerthsen et al., *Physik* 16:868-870.

EP Patent Application Publication No. 2 006 786 discloses visualizing a BG risk index, a measure for an overall risk of extreme blood glucose over time in the form of a phase space diagram.

EP Patent No. 1 702 559 discloses a method and a system for analyzing glucose metabolism; however, it is not concerned with actually measuring a glucose concentration but to a processing of data points. The data points may be processed by plotting a graphic phase space representation that may be provided to a physician as diagnostic aid. A function of the blood glucose concentration and/or at least one of its derivatives with respect to time may be used as phase space coordinates. The glucose concentration or a rate of change of the glucose concentration may be one of the phase space coordinates. A trajectory in phase space described by a sequence of data points may be analyzed to determine a disturbance parameter. The disturbance parameter may indicate which state of a disease of glucose metabolism is likely to be manifest. With progress of an illness, a regulation mechanism for an adjustment of the blood glucose concentration may be useful.

U.S. Pat. No. 6,448,067 discloses a method and an apparatus for determining a chemical component from a sample, where the sample is measured on a test strip with the help of a color reaction. The method concerns finding the measurement time for measuring the reflection of the test strip. When a function reaches a predetermined value, the method calls for determining a measuring time, and determining from a reflection value measured at the measuring time a content of the chemical component in the sample, preferably the glucose content of a blood sample.

US Patent Application Publication No. 2009/0177406 discloses a slope-based compensation. A biosensor system determines an analyte concentration from an output signal generated from a light-identifiable species or a redox reaction of the analyte. The biosensor system adjusts a correlation for determining analyte concentrations from output signals with one or more index functions extracted from the output signals. The index functions determine at least one slope deviation value or normalized slope deviation from one or more error parameters. The slope-adjusted correlation between analyte concentrations and output signals may be used to determine analyte concentrations having improved accuracy and/or precision from output signals including components attributable to bias.

One or more slope deviation values may be determined that are responsive to one or more errors. Slope deviation values may be determined for temperature, hematocrit, and other contributors. In one example, the analyte generates output signals in response to a pulse sequence of a gated amperometry electrochemical analysis. A ratio parameter may represent a relationship between current generated by the analyte in response to two pulses of a gated amperometry pulse sequence. A %-bias of a measured analyte concentration in a biological fluid may be determined from or correlated with the output signals of the analysis, such as the intermediate currents generated by the analyte in response to a gated amperometry sequence. Output signals may be currents or potentials generated from the sample that are responsive to the input signal. Signals that are near or partially linear may be used. The %-bias in the correlation of analyte concentrations with output signals may be represented by one or more slope deviations obtained from one or more error parameters. Index functions may compensate the measured analyte concentration for one or more errors in the analyte concentration analysis. One or more index functions may be used. Index functions may be experimentally determined as regression equation. The compensation or correction of the analyte concentration value may be started with the error parameter accounting for the largest error in the output signal.

After compensating for the largest effect, any error remaining may be compensated or corrected with additional error parameters independent of the parameter responsive to the largest error. Successive corrected analyte concentration values may be determined using additional index functions, the bias in the determined concentration values may decrease until the bias level approaches the random noise level of the analysis.

Intl Patent Application Publication No. WO 2006/138226 discloses an arrangement and an algorithm for calculating the concentration of an analyte contained in a sample. Therein, a color change rate of a test chemical is detected, and a hematocrit is derived from the color change rate. An appropriate correction factor indicative of hematocrit is used for correcting a glucose concentration.

A known test element may be the one used with the Accu-Chek® Active system by Roche Diagnostics Deutschland GmbH.

U.S. Pat. No. 5,420,042 discloses a method of analytically determining the concentration of a component of a medical sample, in which a reaction of the sample with reagents leads to a time-dependent change in a measured quantity. Therein, the concentration correlates according to an evaluation curve with an input variable derived from a time-dependent change, where the calibration curve is ambiguous for at least a portion of the possible values of the input variable. To obtain an unambiguous correlation to a particular concentration, a training run and an analysis run are separately performed.

Intl Patent Application Publication No. WO 2011/131490 discloses a method of determining an analyte activity or concentration in a sample, particularly an automated algorithm for the quality control of reactions. Therein, plotting the fluorescence intensity of a reporter dye divided by the fluorescence intensity of a passive reference dye against the cycle number leads to a so-called sigmoid function, which is characterized by a background phase, an exponential growth phase and a plateau phase. Since the fluorescence intensity as a function of cycles relates to the initial number of template molecules in the sample, the curves can be used to quantify the amount of fragments in the sample by determination of a specific value.

US Patent Application Publication No. 2008/0070234 discloses a method of quantitatively determining an analyte in a sample. Therein, at least two calibration graphs are provided, where the calibration graphs have been generated by reacting in each case the same analyte-specific substance with different amounts of in each case the same test analyte for in each case a predetermined reaction time.

Intl Patent Application No. WO 2012/084194 discloses a method of determining an analyte concentration, wherein a first electrical potential excitation pulse to a body fluid sample in an analyte sensor is applied, and wherein a first current response of the body fluid sample to the first pulse is recorded. Thereafter, a second excitation pulse is applied to the body fluid sample in the analyte sensor, and a second current response of the body fluid sample to the second pulse is recorded. An analyte level in the body fluid sample is determined by compensating for sources of error based on the first current response to the first pulse.

US Patent Application Publication No. 2007/0235346 A1 discloses a method and a device for determining an analyte concentration in a physiological sample. For this purpose, an electrochemical signal based on a reaction taking place inside an electrochemical cell is recorded, from which a preliminary analyte concentration is derived. The preliminary concentration is then multiplied by a hematocrit correction factor to obtain the constituent concentration in the sample, where the hematocrit correction factor is a function of the electrochemical signal.

A measurement of glucose may be influenced by different hematocrit values. In known methods and devices, a point of time development of a remission signal, e.g. a kinetic curve, may be determined wherein at this point the gradient of the kinetic curve after wetting may decrease under a predetermined value (e.g., 2%/s). This criterion also is known as final value criterion or end value criterion. A remission value at this point in time, an end value, may be used in relationship to a value (e.g., a remission value) before the wetting (e.g., a blank value). A ratio between these two values such as, for example, a relative remission, may be used in combination with a calibration curve such as, for example, a code curve, for determining a glucose value (e.g., a glucose concentration.

These kinds of methods are disclosed in Intl Patent Application Publication No. WO 2008/135128. In particular, this document describes an analysis device with a test carrier for a photometric determination of an analyte in a body fluid. A control value of a control parameter is detected at one detection point during a processing after a calculation step, an error in the measurement and evaluation unit is recognized if the deviation of the control value from the expected value exceeds a predefined threshold value.

In such known methods and devices used in connection with analytical test systems, a propagation in time of a measuring signal, which may be observed after an intake or a sample application usually does not necessarily only have a dependency on the observed analyte, in particular on a presence and/or on a concentration of the analyte (e.g., it can be experimentally observed that in the context of a cNAD-developing, one-way test strips for detecting a glucose concentration in blood, a time propagation of a remission may also be dependent on a temperature such as on a temperature being present during a measurement, and probably also on an air humidity during the measurement and/or on a concentration of hematocrit of the sample). For example, the end value of a remission measurement may depend on the temperature. According to prior art, the end value of a remission measurement may be used to derive a glucose concentration by using a calibration curve. For example, a temperature dependency for a glucose concentration of 250 mg/dL may be more than 2% per Kelvin.

The measurement signal also may be dependent on different other state variables such as, for example, on a storage time of a reagent kit, on a storage time of the test strip, on a "history" of the test strip, and/or on the current state of the test strip. An example may be a change of a dry test chemical caused by or after one or more re-moisturizations. Properties of the measurement signal and/or another signal may be influenced by substances such as acetylsalicylic acid and/or citric acid, which may disturb the signal and/or the measurement signal. Alternatively or additionally, similar analytes may change the signal and/or the measurement signal in a noticeable way, where the similar analytes may be maltose and/or xylose. This may cause interferences and/or errors.

A main disadvantage of methods known from prior art may be, that the end value may not only be dependent on the glucose concentration but also on at least one more state variable as discussed above. There may be a deviation of a glucose value determined by using the end value criterion from a desired value for different concentrations of hematocrit. A prediction of a glucose concentration according to known methods may include deviations being dependent on hematocrit.

For the foregoing reasons, there is a need for methods and devices that at least partially avoid the disadvantages and shortcoming of many known systems and methods. Specifically, it is an object of the present disclosure to provide methods and devices that enable analyte detecting in a body fluid sample, where the analyte detection of the analyte may be less influenced by state variables such as, for example, at least one temperature and/or at least one air humidity and/or a hematocrit concentration and/or a history of a test element.

BRIEF SUMMARY

An inventive concept described herein includes correcting or compensating for effects of state variables on analyte concentrations obtained from electrochemical and/or optical testing. This inventive concept is achieved by providing a set of at least two different evaluation rules adapted to derive a characteristic value from, for example, an optical measurement curve, and then performing at least one multivariate analysis of the characteristic values, which are used to derive an estimate value for at least one target variable Y of the state variables and then determining the analyte concentration by using at least one target variable Y. This inventive concept can be incorporated into exemplary methods, computer programs and devices as described herein and in more detail below.

For example, methods are provided for detecting or determine an analyte concentration in a body fluid sample that can account/correct/compensate for at least one state variable. Briefly, the methods can include the following steps:

Step a): providing at least one optical measurement curve, where the optical measurement curve contains a plurality of measurement values recorded by monitoring a time development of at least one measurement value indicating a progress of a detection reaction between at least one test substance and the body fluid sample. Here, the measurement values contained in the optical measurement curve can be acquired at differing points in time. In addition, the detection reaction is known to be influenced by a set of state variables. Moreover, each state variable characterizes at least one of a state of the body fluid sample and a condition of the detection reaction;

Step b): providing a set of at least two different evaluation rules, each evaluation rule being adapted to derive a characteristic value from the optical measurement curve, thereby deriving a set of characteristic values $X=\{X_i\}_{i=1 \ldots N}$ from the optical measurement curve. Here, the set of characteristic values includes at least one first characteristic value being derived from the optical measurement curve by using at least one first evaluation rule from the set of evaluation rules and at least one second characteristic value being derived from the optical measurement curve by using at least one second evaluation rule from the set of evaluation rules. In addition, the second evaluation rule is different from the first evaluation rule.

Step c): performing at least one multivariate analysis of the at least one first characteristic value and the at least one second characteristic value by using at least one predetermined multivariate evaluation algorithm. The multivariate evaluation algorithm is an algorithm adapted to derive at least one result from at least two variables. Here, the at least one first characteristic value and the at least one second characteristic value are used as the at least two variables, thereby deriving at least one estimate value for at least one target variable Y of the state variables.

Step d): determining at least one analyte concentration by using the at least one target variable Y.

In the methods, at least one of the steps, may be performed by using at least one computer.

In the methods, the state variables can be a composition of the body fluid sample such as a content of at least one component of the body fluid sample including at least one analyte concentration; a content of at least one particulate component of the body fluid sample such as a hematocrit; a temperature of the body fluid sample; a humidity of an ambient atmosphere surrounding the body fluid sample; a storage time of the test substance; a storage time of a test element incorporating the test substance; an interfering substance such as ascorbate; or even alterations of the sample or of certain properties of the sample caused by pharmacological treatment of a donor of the sample. In some instances, the particular component is a hematocrit.

The composition of the body fluid sample may include different contents of at least one component. The composition of the body fluid sample may include variations of the sample from an average composition of a sample. The composition of the sample may even include variations of concentrations of blood components (e.g., a hematocrit value being higher or lower as in average blood samples).

Likewise, the set of characteristic values may contain about 2-20 characteristic values or even about 3-10 characteristic values. Alternatively, even more characteristic values may be possible. It may be advantageous to minimize the number of characteristic values for saving storage space and/or for simplifying the calculation and/or for saving calculation time.

Moreover, the target variable Y may include the at least one analyte concentration in a body fluid sample. In some instances, the target variable Y may include the glucose concentration and/or the hematocrit concentration.

Also provided are methods of characterizing a body fluid sample. Briefly, the methods can include the following steps:

Step A): bringing the body fluid sample into contact with at least one test substance, thereby initiating a detection reaction of the test substance and the body fluid sample, wherein the detection reaction is known to be influenced by a set of state variables, each state variable characterizing at least one of a state of the body fluid sample and a condition of the detection reaction.

Step B): monitoring a time development of at least one measurement value indicating a progress of the detection reaction, thereby recording an optical measurement curve containing a plurality of the measurement values acquired at differing points in time.

Step C): evaluating the optical measurement curve by using the methods disclosed above.

In view of the foregoing, computer programs are provided that can include computer-executable instructions for performing the method above when the program is executed on a computer or computer network.

Likewise, devices, such as sample analysis devices for characterizing a body fluid sample, are provided that can include at least one measuring unit for measuring a detection reaction of at least one test substance and at least one body fluid sample, where the detection reaction influenced by a set of state variables as described herein. In some instances, the measuring unit is adapted for monitoring a time development of at least one measurement value indicating a progress of the detection reaction, thereby recording an optical measurement curve containing a plurality of the measurement values acquired at different points in time.

The devices also can include at least one evaluation device for evaluating an optical measurement curve and for analyzing the at least one body fluid sample. The at least one evaluation device including at least one evaluation unit adapted to perform the methods disclosed herein.

In some instances, the devices also include at least one test element having at least one test substance adapted to perform the detection reaction.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
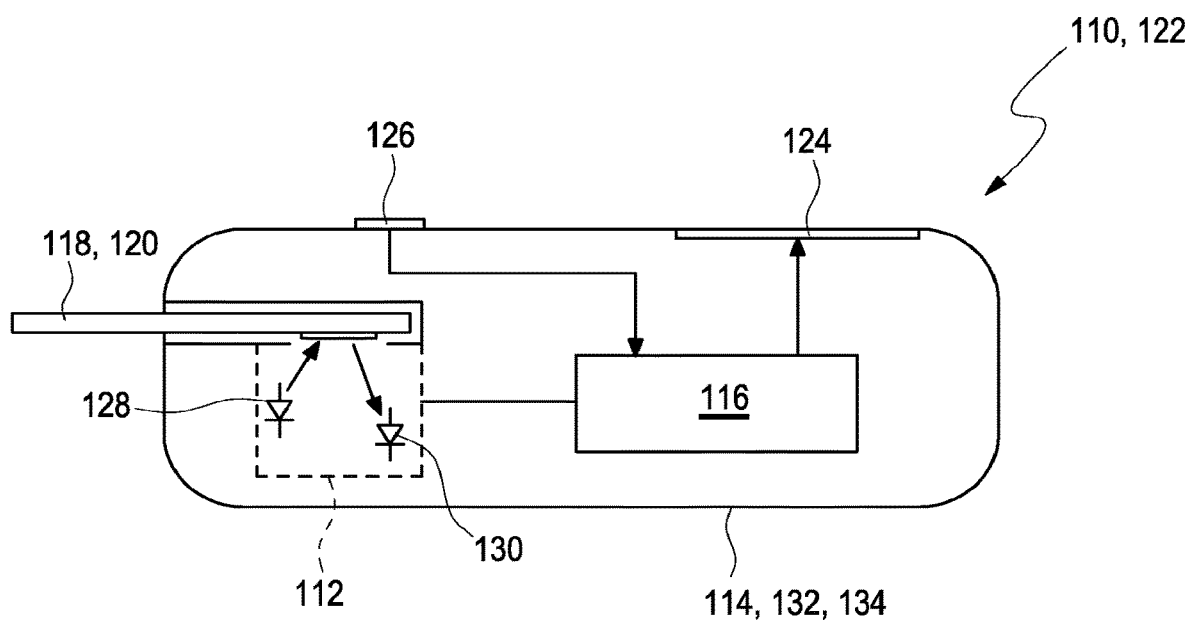
FIG. 1 shows a schematic view of an exemplary sample analysis device.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, computer programs and devices now will be described more fully hereinafter with reference to the accompanying drawings, in which some, but not all embodiments of the inventive concept are shown. Indeed, the methods, computer programs and devices may be embodied in many different forms and should not be construed as limited to the embodiments set forth herein; rather, these embodiments are provided so that this disclosure will satisfy applicable legal requirements.

Likewise, many modifications and other embodiments of the methods, computer programs and devices described herein will come to mind to one of skill in the art to which the disclosure pertains having the benefit of the teachings presented in the foregoing descriptions and the associated drawings. Therefore, it is to be understood that the methods, computer programs and devices are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, computer programs and devices, the preferred methods and materials are described herein. Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

State variables can significantly influence an analyte concentration result during body fluid sample analysis. State variables may be a variable characterizing at least one of a state of the body fluid sample, of the test substance, of a test strip, and/or a condition of the detection reaction. Examples for a state variable may be the analyte concentration in a body fluid sample (e.g., a concentration of glucose); a content of at least one component of the body fluid sample (e.g., a content of a particulate component such as hematocrit); a temperature of the body fluid sample; a humidity of an ambient atmosphere surrounding the body fluid sample; a storage time of the test substance; a storage time of the test element; an illumination of an environment of the detection reaction and/or of the test element; a volume of the body fluid sample. Thus, the state of the body fluid sample may be a temperature of the body fluid sample and/or a humidity of the body fluid sample, a volume of the body fluid sample, an age of the body fluid sample, a storage time of the body fluid sample, and/or a purity of the body fluid sample. In this manner, a condition of the detection reaction may include a state of an environment of the test chemistry and/or a property of the detection reaction. The condition of the detection reaction may include a temperature during the detection reaction and/or a temperature change during the detection reaction and/or a humidity during the detection reaction and/or a presence of a catalyst during the detection reaction.

The methods, computer programs, and devices disclosed herein may provide a large number of advantages over known methods, computer programs and devices. In particular a detection of an analyte in a body fluid sample may be performed more accurately, especially with smaller errors and even with less influence by different state variables when compared to known methods, computer programs and devices. For example, the inventive concept may be used to distinguish between influences on a measurement curve, especially on an optical measurement curve, caused by different state variables. In particular, the use of the multivariate analysis may significantly reduce deviations of measured concentrations of glucose caused by high, fluctuations of hematocrit concentration and/or temperature changes.

The methods, computer programs and/or devices may enable at least a suppression of influences caused by at least one state variable when detecting an analyte in body fluid sample, especially without accepting influences of other state variables. In particular, an influence of the hematocrit concentration when detecting a glucose concentration may be suppressed without accepting an influence of the temperature.

Likewise, the multivariate analysis may enable an isolation of different influencing parameters (e.g., different state variables) when detecting an analyte in a body fluid sample, especially when determining a glucose concentration.

Moreover, the multivariate analysis may enable a parallel instead of a sequential analysis of the body fluid sample. As disclosed herein, a calculation of a glucose concentration and a correction of this concentration (e.g., a correction from influences by a hematocrit concentration) may be executed in one, or in one not separable, step. For example, a global minimum of the deviations between a prediction and a reference value of the analyte concentration (e.g., in forms of chi-squared), which itself is influenced by the glucose concentration and/or by the hematocrit concentration may be searched in one single step by using, for example, PLS. Here, only one single value for the analyte concentration may be involved. The analyte concentration therefore may be determined in an iterative multidimensional way, where the respective multidimensional space may be spanned by the characteristic values, especially by a first characteristic value and by a second characteristic value. The characteristic values may be determined by using a remission measurement. Advantageously, a correction from a hematocrit concentration may not depend on the glucose concentration.

Methods

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps. Likewise, one of the steps or a plurality of the steps or even all of the steps may be performed by using a data processing device such as a computer, preferably a microcomputer and/or an application-specific integrated circuit (ASIC).

Methods incorporating the inventive concept firstly can include methods of detecting or determining an analyte concentration/presence in a body fluid sample that account for at least one state variable.

As used herein, "detecting" means a process of generating information on the presence of the analyte in the body fluid sample. The information preferably may be quantitative information (i.e. information on an analyte concentration). Therein, the concentration generally may be given in arbitrary units, referring to an amount of the analyte per amount of the body fluid sample (e.g., in absolute units and/or as a percentage). The amount of the analyte may be given in mass units and/or mol and/or volume units. Typical examples of units of concentrations may be: mg/dl (milligrams per deciliters) and/or mg/kg (milligrams per kilograms) and/or % by weight and/or vol.-%. Other units may be possible. "Determining" is used in a similar manner.

Briefly, the methods can include the following steps:

Step a): providing at least one optical measurement curve, where the optical measurement curve contains a plurality of measurement values recorded by monitoring a time development of at least one measurement value indicating a progress of a detection reaction between at least one test substance and the body fluid sample. Here, the measurement values contained in the optical measurement curve can be acquired at differing points in time. In addition, the detection reaction is known to be influenced by a set of state variables. Moreover, each state variable characterizes at least one of a state of the body fluid sample and a condition of the detection reaction.

As used herein, "monitoring a time development" means a process of acquiring a plurality of measurement values at different measurement times. During monitoring, a time development, the measurement curve, especially at least the optical measurement curve, may be generated. The monitoring of the time development may solely include acquiring the measurement values, without acquiring the additional information of the measurement times of the respective measurement values. Thus, for example, this option may be feasible when using a constant acquisition frequency. Alternatively or additionally, the monitoring of the time development may include acquiring the respective measurement times, thereby generating the measurement curve, especially the optical measurement curve, including data pairs $(R_i, t_i)$ and/or $(t_i, R_i(t_i))$.

As used herein, "detection reaction" means an arbitrary type of chemical reaction of at least one test substance and a body fluid sample having or suspected of having the at least one analyte of interest. For example, reference may be made to the test substances disclosed in the prior art documents cited above. Additionally or alternatively, other types of test substances may be used. The detection reaction may be adapted to generate a measurement value and/or to generate a change in time of the measurement values and/or to generate analysis information. In some instances, the detection reaction may be a chemical reaction between at least one component of the test substance that may be adapted to indicate a presence and/or a concentration of the at least one analyte in the body fluid. Thus, generally, the test substance may be a chemical compound and/or a chemical mixture adapted to react with the at least one analyte to be detected, especially in a highly analyte-specific fashion. The detection reaction may be embodied such that a test substance may react with the at least one analyte to be detected and, thereby, may fully or in part change by itself (e.g., may transform into another chemical species and/or may transform its surrounding in a detectable way), which may be measured, thereby deriving the plurality of measurement values and the measurement curve, especially the optical measurement curve. The progress of the detection reaction may be indicated by at least one physical measurement value and/or a change in at least one physical measurement value, which may be used as the measurement value. In some instances, the detection reaction may be an optically detectable detection reaction, which may be optically observable, such as by using a reflection measurement and/or a transmission measurement. Other types of optical measurements may be feasible.

As used herein, "test substance" means a chemical compound or substance or a mixture of two or more chemical compounds or substances adapted for performing the detection reaction, especially an analyte-specific detection reaction, most preferably an optically observable detection reaction. In some instances, the test substance may include one or more enzymes adapted to react with the at least one analyte to be detected. Additionally, the test substance may include one or more auxiliary components such as, for example, mediators and/or co-enzymes. For test substances that also be used herein, reference may be made to the test substances known from prior art, such as the cNAD test substances. Moreover, the test substance may include one or more test chemicals.

As a first example of a test chemical that may be used herein, reference is made to the so-called "PQQ chemistry," which is disclosed in EP Patent Application Publication No. 0 354 441. Such as test chemical may contain a PQQ-dependent dehydrogenase and a direct electron acceptor that may be an aromatic nitroso compound or an oxim. Further, one or more indicators may be present, such as one or more dyes such as, for example, heteropoly blue indicator (as disclosed in EP Patent Application Publication No. 0 431 456.

As a second example of a test substance that may be used herein, reference is made to the so-called "cNAD chemistry," as disclosed in Intl Patent Application Nos. WO 2007/012494, WO 2009/103540, WO 2011/012269, WO 2011/012270 and WO 2011/012271. For example, Intl Patent Application Publication No. WO 2007/012494 discloses cNAD derivatives; Intl Patent Application Publication No. WO 2009/103540 discloses stabilized enzyme/coenzyme complexes; and Intl Patent Application Publication Nos. WO 2011/012269, WO 2011/012270 and WO 2011/012271 disclose the synthesis of cNAD and cNAD/derivatives as well as intermediates/precursors.

Additionally or alternatively, other types of test substances may be used.

As used herein, "differing points in time" means that at least two of the measurement values may be recorded at different points in time. The optical measurement curve may include discrete measurement values for different points in time. Alternatively, the optical measurement curve may be continuous in time. The optical measurement curve may be generated by extrapolation of discrete measurement values by using at least one theoretical model and/or by using at least one fitting method.

The monitoring of the time development of the at least one measurement value indicating the progress of the detection reaction may be adapted to be an impact-free monitoring of the detection reaction without influencing the detection reaction. As used herein, "impact-free monitoring" means a detection reaction without changes of properties of an environment of the detection reaction. The detection reaction may be observed without changes of temperature and/or changes of humidity and/or changes of at least one of the state variables.

The optical measurement curve may be an amount of data characterizing a time development of a detection reaction. The optical measurement curve may contain a plurality of measurement values recorded at differing points in time. The optical measurement curve optionally or additionally may contain the respective measurement times of the measurement values, such as by containing data pairs $(R_i, t_i)$ and/or $(t_i, R_i(t_i))$. The optical measurement curve may be a measurement curve including measurement values representing an optical physical quantity. The optical measurement curve may include a plurality of measurement values selected from: remission values; relative remission values; transmission values; absorption values; fluorescence values; intensity values; frequency values; spectroscopic values; spectral values; coherence values; decoherence values; photon numbers.

The measurement value may be a quantifiable measurement result $R_i$, recorded by at least one arbitrary measurement method based on at least one of a physical and/or chemical and/or biological measurement principle, especially an optical measurement principle such as a reflection measurement, a fluorescence measurement, or any other type of optical measurement. The measurement method may be selected from: light detection (e.g., by at least one photodiode and/or by at least one CCD camera); spatial light detection (e.g., by at least one CCD camera); light frequency measurements (e.g., by spectroscopy and/or by a light beating method, especially combined with a Fourier analysis); comparisons of a color of at least a part of a test element with at least one reference color bar; measurements of an intensity with an optical power meter; measuring a frequency by using a wavemeter; or analysis of camera images.

In general, the body fluid may be selected from: blood, interstitial fluid, urine, plasma, serum and saliva. Other body fluids may be possible. Additionally, the body fluid may be prepared by adding at least one additional component. Furthermore, the body fluid may be prepared by heating or cooling or shaking.

Step b): providing a set of at least two different evaluation rules, each evaluation rule being adapted to derive a characteristic value from the optical measurement curve, thereby deriving a set of characteristic values $X=\{X_i\}_{i=1 \ldots N}$ from the optical measurement curve. Here, the set of characteristic values includes at least one first characteristic value being derived from the optical measurement curve by using at least one first evaluation rule from the set of evaluation rules and at least one second characteristic value being derived from the optical measurement curve by using at least one second evaluation rule from the set of evaluation rules. In addition, the second evaluation rule is different from the first evaluation rule.

As used herein, "different evaluation rules" means that an algorithm of the first evaluation rule may differ from the algorithm of the at least one second evaluation rule in at least one coefficient and/or in at least one parameter and/or in at least one other component defining the algorithm. "Different evaluation rules" may include that the algorithm of the first evaluation rule may differ from the algorithm of the second evaluation rule only in a point in time (e.g., in the parameter t). Thus, two evaluation rules may differ from each other just by the difference of the time parameter t. Alternatively, the two evaluation rules may differ from each other by applying two different components related to the algorithm, such as two different thresholds or two different change rates below a predetermined threshold.

An evaluation rule may be a rule for directly or indirectly deriving at least one characteristic value from the measurement curve, especially from the optical measurement curve. According to the methods, at least two (2) different evaluation rules are used, which are applied to one and the same optical measurement curve and/or one and the same measurement curve to derive the at least two characteristic values from the optical measurement curve and/or from the measurement curve, especially from one and the same optical measurement curve. The evaluation rule generally may be an arbitrary mathematical algorithm or may be an arbitrary combination of algorithms for deriving one or more numeric values from the optical measurement curve and/or from the measurement curve (e.g., from at least one part of the measurement curve or of the optical measurement curve such as from one time interval of the measurement curve or of the optical measurement curve or from at least one curve, curve part or data derived from the optical measurement curve and/or from the measurement curve).

At least one of the evaluation rules may be and/or may include the end value criterion as described above. Alternatively, the evaluation rule may be different from the end value criterion. For example, the first evaluation rule and/or the second evaluation rule may not comprise an end value criterion.

In any event, the first evaluation rule may not be transformed into the second evaluation rule by a time transformation. In some instances, the first evaluation rule may not be transformable into the second evaluation rule by a time transformation, especially not by a linear time transformation. The time transformation may include a change of a point in time. The first evaluation rule may not just be different from the second evaluation rule by application of identical algorithms for different times t. The first evaluation rule and the second evaluation rule may have different algorithmic components or may include different parameters, where the parameter is not the time t or a point in time.

The characteristic value may be a specific numeric value derived from the optical measurement curve and/or from the measurement curve by using at least one evaluation rule, preferably by using one evaluation rule. The characteristic value therefore may be a correlation coefficient and/or a concentration. Likewise, the set of characteristic values may contain about 2-20 characteristic values or even about 3-10 characteristic values. Alternatively, even more characteristic values may be possible. It may be advantageous to minimize the number of characteristic values for saving storage space and/or for simplifying the calculation and/or for saving calculation time.

As used herein, "about" means within a statistically meaningful range of a value or values such as, for example, a stated concentration, length, width, height, angle, weight, molecular weight, pH, sequence identity, time frame, temperature, value or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

N may be a natural number, especially an arbitrary natural number. The second evaluation rule may differ from the first evaluation rule just by a point in time. Additionally or alternatively, the second evaluation rule may differ from the first evaluation rule by at least one parameter being different from the point in time and/or by at least one different algorithm. As a particular example, N may be selected as 3, such that a third evaluation rule may be provided, where the third evaluation rule may be different from both, the first evaluation rule and the second evaluation rule. Hereby, it is contemplated that the algorithm of the first evaluation rule may differ from the algorithm of the second evaluation rule only in a point in time such as, for example, in the parameter t. Alternatively, the two evaluation rules may differ from each other by any other feature as described above or below. Within this particular embodiment, the at least one first characteristic value may be derived from the first evaluation rule according to step c). However, during step c), and as explained in further detail below, depending on the at least one first characteristic value, such as its absolute value, its relative value, and/or a predetermined range wherein the at least one first characteristic value may be found inside or outside, either the second evaluation rule or the third evaluation rule may be used in a further calculation employing the multivariate evaluation algorithm.

In some instances, the at least two evaluation rules may be adapted to derive the characteristic values from at least two derivatives of the optical measurement curve. A derivative may be a derivative of arbitrary order. The derivative may be a 0-th order derivative. Likewise, at least one of the derivatives may be a higher order derivative, thus, a first derivative, a second derivative or a higher order derivative. For example, the first evaluation rule may be used for generating the first characteristic value out of a n-th derivative of the optical measurement curve or of the measurement curve. n may be higher or equal to zero, preferably higher or equal to one. The second evaluation rule preferably may be used to generate the second characteristic value out of a m-th derivative of the optical measurement curve or of the measurement curve. m may be higher or equal to zero, preferably higher or equal to one. In some instances, n may be different from m. The 0-th order derivative may be the identity of the optical measurement curve or of the measurement curve. The first derivative of the optical measurement curve or of the measurement curve may be the slope of the optical measurement curve or the slope of the measurement curve.

The at least two derivatives may be derivatives including at least two derivatives of different order. For example, the first evaluation rule may be a first derivative of the optical measurement curve and the second evaluation rule may be a second derivative of the optical measurement curve.

In some instances, the derivatives may be generated by using at least one filtering algorithm such as a Savitzky-Golay filtering algorithm. The filter algorithm may be a numerical filtering algorithm. The filtering algorithm may be an algorithm being able to derive and/or generate at least one of the derivatives. Other types of algorithms may be possible.

The first characteristic value therefore may be determined by using a first time interval of the optical measurement curve. The second characteristic value may be determined by using a second time interval of the optical measurement curve. The first time interval of the optical measurement curve may be different from the second time interval of the optical measurement curve. Alternatively, the first characteristic value may be determined by using a first time interval of a measurement curve, where the second characteristic value may be determined by using a second time interval of the measurement curve, where the first time interval of the measurement curve may be different from the second time interval of the measurement curve. The first time interval may overlap with the second time interval. Alternatively, the first time interval may be completely separated from the second time interval. A time interval (e.g., the first time interval and/or the second time interval) may be an interval in time that includes at least two measurement values.

In step b), the evaluation rules may be adapted such that the characteristic values may be linearly independent, thereby generating unique solutions for the numeric values of the coefficients. Alternatively, the evaluation rules may be adapted such that the characteristic values may be not linearly independent.

At least one of the two different evaluation rules may be selected from:

a. using a specific measurement value of the optical measurement curve or a derivative of the optical measurement curve at a predetermined point in time as the characteristic value, especially using one or more specific criteria, particularly using one or more specific conditions, which may include at least one end value criterion such as a change rate below a predetermined threshold value;

b. using a mean value of the optical measurement curve or a derivative of the optical measurement curve over a predetermined period of time as characteristic value;

c. using a characteristic point in time of the optical measurement curve or of a derivative of the optical measurement curve as the characteristic value, especially a characteristic point in time at which one or more of the following occur: (i) a maximum of the optical measurement curve or of a derivative of the optical measurement curve; (ii) a minimum of the optical measurement curve or of a derivative of the optical measurement curve; or (iii) an inflection point of the optical measurement curve or of a derivative of the optical measurement curve;

d. using a characteristic parameter of the optical measurement curve or of a derivative of the optical measurement curve as the characteristic value, especially a characteristic parameter at one of: (i) a maximum of the optical measurement curve or of a derivative of the optical measurement curve; (ii) a minimum of the optical measurement curve or of a derivative of the optical measurement curve; or (iii) an inflection point of the optical measurement curve or of a derivative of the optical measurement curve;

e. using a fit parameter derived by at least one fitting process as the characteristic value, where the fitting process may imply a fitting of at least one predetermined fit curve to at least a section of the optical measurement curve or of a derivative of the optical measurement curve; and f. using at least one value derived from a phase plot of at least two derivatives of different order of the optical measurement curve as the characteristic value, where the phase plot may include at least one phase space curve, and where the value derived from the phase plot may be selected from: (i) a position of a center of the phase space curve; (ii) a length of the phase space curve; (iii) a phase space volume; (iv) a phase space area; (v) a point with a maximal distance to the center of the phase space curve; or (vi) a mean squared distance from the origin of the phase space.

The specific measurement value may be a measurement value correlating or anti-correlating with at least one of the target variables. For example, the specific measurement value may be a measurement value correlating or anti-correlating with at least one of the state variables. The pre-determined point in time may be a fixed point in time or a point in time which may be deter-mined by using one or more specific criteria, such as by using one or more specific conditions. The specific criteria or the specific conditions may comprise at least one change rate below a predetermined threshold value (e.g., an end value criterion, such as 2%/s or 1%/s).

The mean value of the optical measurement curve may be a mean value of the whole optical measurement curve or a mean value of a part of the optical measurement curve. The mean value may be an arithmetic mean or a geometric mean or a harmonic mean or another mean or average. The derivative may be a derivative as defined above. The mean value may be a mean value over a predetermined period of time. The predetermined period of time may comprise at least two measurement values. The predetermined period of time may comprise at least two measurement values lying next to each other.

The characteristic point in time may be a fixed point in time or a point in time which may be determined by using one or more specific criteria, such as by using the end value criterion. The fitting process may be an arbitrary fitting process such as, for example, a polynomial and/or a linear fitting process and/or an exponential fitting process.

The position of a center of the phase space curve may comprise preferably the coordinates of the center of the phase space curve. The shape of the phase space curve may depend on the state variables, e.g. on the concentration of glucose and/or on the temperature and/or on the concentration of hematocrit.

In addition, step b) may include generating a set of evaluation rules. The generating of the set of evaluation rules may include the following sub-steps:

Sub-step b1): providing a learning set of learning measurement curves, acquired by using a learning set of learning body fluids and by monitoring detection reactions of the test substance and the test body fluids. The test body fluids and the detection reactions may be chosen such that the learning measurement curves may be acquired with different sets of state variables;

Sub-step b2): identifying a set of candidate evaluation rules and deriving a set of candidate characteristic values from the learning set of learning measurement curves;

Sub-step b3): determining a correlation between the candidate characteristic values for each candidate evaluation rule and the state variables; and Sub-step b4): selecting the set of evaluation rules from the set of candidate evaluation rules by accounting for correlations determined in sub-step b3).

As used herein, "learning body fluid" means a body fluid having a known set of state variables as long as these state variables refer to properties of the body fluid, such as a known temperature, a known analyte content or concentration, such as a known glucose concentration, and a known hematocrit. Consequently, "learning measurement curve"

may refer to a measurement curve acquired by using a learning body fluid and by using a known set of state variables. Therein, the known state variables may be defined by the learning body fluid as long as these state variables refer to properties of the learning body fluid, and may be defined by properties and/or circumstances of the measurement as long as these state variables are defined by the measurement, such as state variables referring to details of the detection reaction and/or the test substance. Further, "learning set of learning body fluids" means a set comprising a plurality of learning body fluids having different known sets of state variables. As used herein, "learning set of learning measurement curves" means a set of learning measurement curves acquired by using different sets of known state variables.

The candidate evaluation rule may be an arbitrary evaluation rule that may be arbitrarily chosen out of all potential evaluation rules. In some instances, the candidate evaluation rules may be chosen by using expert knowledge, such as by starting with candidate evaluation rules that have proven to lead to candidate characteristic values which highly, such as by having a correlation coefficient exceeding a predetermined threshold, correlate with one or more of the state variables, especially with one specific target variable, for similar body fluid and/or similar measurement conditions. In addition, correlation coefficients for a large number of candidate evaluation rules may be compared visually. For example, expert knowledge and/or experience may be used regarding candidate evaluation rules that have proven to show a high correlation coefficient with one state variable, such as a target variable, whereas showing a low correlation coefficient, such as the correlation coefficients below a predetermined threshold, for other state variables, especially for all other state variables for similar body fluids and/or similar measurement conditions. Additionally or alternatively, instead of the correlation coefficients themselves, expert knowledge and/or experience regarding their Merit values may be used.

The candidate characteristic value may be a candidate value derived from a learning measurement curve by using a candidate evaluation rule. As used herein, "correlation" may refer to any of a broad class of statistical relationships. The correlation may be a dependence, which may be a statistical relationship between two variables and/or between two sets of data.

Sub-step b3) may include determining at last one correlation parameter for each candidate evaluation rule for each state variable. The correlation parameter preferably may be a Pearson correlation coefficient. A correlation parameter may be a correlation coefficient. The correlation parameter and/or the correlation coefficient and/or the Pearson correlation coefficient may be a numerical value for a degree of correlation. The most common correlation coefficient is the Pearson correlation coefficient. The Pearson correlation coefficient preferably may be a correlation coefficient being sensitive only to a linear relationship between the two variables.

In sub-step b4), a Merit value may be calculated for each correlation. The selecting of the set of evaluation rules from the set of candidate evaluation rules may be performed by accounting for the Merit values. The Merit value may be derived out of the correlations and/or the correlation coefficients out of the correlation values, especially out of the Pearson correlation coefficients by, for example, using the formula:

$$\text{Merit value} = \frac{\text{correlation}^2}{(|\text{correlation}_{glucose}| + |\text{correlation}_{hematocrit}| + |\text{correlation}_{humidity}|)}.$$

The correlation may be the correlation coefficient for the concentration of glucose correlation$_{glucose}$ or the correlation coefficient for the hematocrit concentration correlation$_{hematocrit}$ or the correlation coefficient for the humidity concentration correlation$_{humidity}$. The Merit value may be used for extracting the characteristic values.

In sub-step b4), a candidate evaluation rule may be determined to be an evaluation rule if the corresponding correlation determined in sub-step b3), may fulfill at least one predetermined condition.

Step c): performing at least one multivariate analysis of the at least one first characteristic value and the at least one second characteristic value by using at least one predetermined multivariate evaluation algorithm. The multivariate evaluation algorithm is an algorithm adapted to derive at least one result from at least two variables. Here, the at least one first characteristic value and the at least one second characteristic value are used as the at least two variables, thereby deriving at least one estimate value for at least one target variable Y of the state variables.

The multivariate analysis may include at least one mathematical operation. A multivariate analysis may be performed of at least two different numeric values. The multivariate evaluation algorithm may be an arbitrary algorithm for deriving at least one numerical result, also referred to as an output, from at least two variables and/or values, preferably from the at least one first characteristic value and the at least one second characteristic value, also referred to as input variables. The multivariate evaluation algorithm may be an algorithm adapted to derive at least one result from the at least two variables. The algorithm may include an arbitrary rule for generating the output by using the at least two input variables. The output may be the target variable Y, and the input variables may be the characteristic values. In some instances, the multivariate evaluation algorithm is or may include at least one equation. At least two variables, especially the first characteristic value and the second characteristic value, may be input variables. The input variables may be used or may be combined in this equation to derive the result. The multivariate evaluation algorithm may include one of a linear equation, a quadratic equation, a cubic equation, or any other polynomial equation using the at least two variables, especially the first characteristic value and the second characteristic value, and a plurality of coefficients, thereby deriving the at least one result.

The multivariate analysis may be a process or a mathematical operation using the multivariate evaluation algorithm and at least two input variables, especially the first characteristic value and the second characteristic value, specifically the characteristic values, for generating at least one numerical result, specifically the estimate value for the at least one target variable. The multivariate evaluation algorithm may be or may include a one-step algorithm in which the first characteristic value and the second characteristic value may be used as input variables for one and the same algorithm, such as using one and the same equation having the first characteristic value and a second characteristic value as input variables. Alternatively, the multivariate evaluation algorithm may be or may include multiple steps, where, step-by-step, two or more algorithms may be successively applied.

The multivariate analysis may be an analysis, and the multivariate evaluation algorithm may be an algorithm as described in Martens & Næs, "Multivariate Calibration" 97-165 (John Wiley and Sons Ltd, 1998) and/or Henrion & Henrion, "Multivariate Datenanalyse" 103-157 (Springer-Verlag, 1995).

The estimate value may be a value of the at least one target variable Y rendered by a method for evaluating the optical measurement curve and/or the measurement curve. The value may be believed to optimally quantify the target variable. The estimate value may be a numeric value. Likewise, the target variable Y may include the at least one analyte concentration in a body fluid sample. In some instances, the target variable Y may include the glucose concentration and/or the hematocrit concentration.

In step c), the predetermined multivariate evaluation algorithm may include at least one polynomial algorithm selected from:

$$Y=A \cdot X, \quad (1);$$

$$Y=X^T \cdot A \cdot X, \quad (2); \text{ and}$$

$$Y=X^T \cdot (X^T \cdot A \cdot X), \quad (3),$$

A may be a one-dimensional, a two-dimensional or a three-dimensional evaluation tensor. In some instances, A may be a symmetric tensor. For example, A may be a 3×3 tensor. X and/or Y may be vectors or matrixes. In some instances, Y is a matrix or a vector that includes different target variables; and X can be a matrix or a vector that includes at least two different characteristic values. Other polynomial algorithms also may be used.

Alternatively, the predetermined multivariate evaluation algorithm may include at least one algorithm selected from:

$$Y=\Sigma_i a_i \cdot X_i, \quad (4);$$

$$Y=\Sigma_i a_i \cdot X_i + \Sigma_{i,j} a_{ij} \cdot X_i \cdot X_j, \quad (5); \text{ and}$$

$$Y=\Sigma_i a_i \cdot X_i + \Sigma_{i,j} a_{ij} \cdot X_i \cdot X_j + \Sigma_{i,j,k} a_{ijk} \cdot X_i \cdot X_j \cdot X_k, \quad (6).$$

$a_i$, $a_{ij}$, $a_{ijk}$ may be predetermined coefficients. i, j and k may be N, mutually independent, integers from 1 to N.

Additionally or alternatively, the predetermined multivariate evaluation algorithm may include a function that may involve a decision tree. As used herein, a "decision tree" means at least one decision branch that may allow selecting one out of at least two, especially two, alternative procedures based on an assessment whether a predetermined condition may be fulfilled or not.

The decision branch itself may include an additional second-order decision branch that may allow performing one out of at least two, especially two or three, further alternative procedures depending on the assessment of a further predetermined condition. In addition, the second-order decision branch may include at least one further higher-order decision branch. In general, the predetermined condition, which may depend on at least one characteristic value, may assess a (non-)existence of a value or whether a definite value falls within a predetermined range or not.

The decision branch may, thus, offer a decision between performing or not performing a specific procedures or performing the specific procedures under a specific parameter, with a specific parameter set, or within a specific parameter range. With regard to the methods disclosed herein, the specific parameter may include the first or the second characteristic value. However, other kinds of predetermined conditions that may especially reflect the specific circumstances of the methods disclosed herein are possible.

As a non-limiting example, the predetermined multivariate evaluation algorithm may include the following function involving a first-order decision tree $f(X_1, X_2)$, $$Y=f(X_1,X_2)=\{g_1(X_2) \text{ for } \text{cond}(X_1); g_2(X_2) \text{ for NOT } \text{cond}(X_1)\}, \quad (7),$$

where, depending on the assessment whether the predetermined condition $\text{cond}(X_1)$, which may depend on the first characteristic value $X_1$, may be fulfilled or not, the estimate value for target variable Y may be derived according to Equation (7) by either using a first function $g_1(X_2)$ or an alternative second function $g_2(X2)$, which both may depend on the second characteristic value $X_2$. Other examples for the predetermined multivariate evaluation algorithm may include more complex structures of the decision tree, such as a second-order decision tree, where depending on the assessment whether a first predetermined condition, which may depend on one of the characteristic values, may be fulfilled or not, a second predetermined condition, which may depend further on another one of the characteristic values, may be assessed until the estimate value for target variable Y may be derived.

Regardless, the at least one multivariate evaluation algorithm may include at least one algorithm selected from: a partial least squares regression algorithm (PLSR); a principal component regression algorithm (PCR); a support vector machine algorithm (SVM); an artificial neuronal network algorithm (ANN) and/or any genetic algorithm (GA).

Step d): determining at least one analyte concentration by using the at least one target variable Y.

As used herein, "determining at least one analyte concentration by using the at least one target variable" may include different options. The target variable Y may be the at least one analyte concentration or may include the at least one analyte concentration. Additionally or alternatively, the target variable Y may be another target variable Y being different from the at least one analyte concentration. The target variable Y may include a target variable Y being different from the at least one analyte concentration. The target variable Y may be or may include a target variable Y being independent from the at least one analyte concentration. For example, the target variable Y being derived in step c) may be the at least one analyte concentration or if the target variable Y derived in step c) includes the analyte concentration, nothing may have to be done in step d), or just a simple calculation. If the target variable Y derived in step c) is not the at least one analyte concentration or does not include the at least one analyte concentration, the at least one analyte concentration may be determined in step d) by using the target variable. For example, a raw value of the at least one analyte concentration may be determined, for example, by using an observable and/or a measurement value.

The raw value may be corrected by using a correction algorithm, where the correction algorithm may use the target variable Y derived in step c). The correction algorithm may be or may include a temperature correction and/or a hematocrit correction. The raw value may be transformed to a corrected value of the at least one analyte concentration by using the correction algorithm. For example, an observable and/or a specific measurement value may be generated out of the optical measurement curve and/or out of the measurement curve by using a known method such as, for example, by using a remission value at an end time value, especially by using a remission end value. The end time value may be the time at which the optical measurement curve such as, for example, a remission curve, may have a slope being smaller than a specific threshold. The threshold may be about 2%/s. The specific measurement value or the remission value may be transformed into the raw value by using a transformation algorithm. The raw value may be transformed into the corrected value by using a second transformation algorithm (e.g., the correction algorithm). Alternatively, a method may be used using only one transformation algorithm in a one-step method, where the measurement value and the at least one target variable Y may be transformed by using the transformation algorithm. The transformation may lead directly to the corrected value of the at least one analyte concentration. The measurement value here may be a remission value being determined out of a measurement curve and/or out of the optical measurement curve at a specific point in time (e.g., the remission end value). Other options may be possible.

The target variable Y may be a state variable of specific interests. The target variable Y may be derived in a method as described herein. Generally, the target variable Y may be or may include an arbitrary state variable. The target variable Y even may change during the evaluation. Thus, one and the same optical measurement curve and/or one and the same measurement curve may be evaluated in order to derive different target variables, even by using the same multivariate evaluation algorithm, which may be one of the major advantages of the present invention. For example, by using the same measurement curve, especially the same optical measurement curve, both the concentration of glucose and the hematocrit may be derived as target variables. Alternatively, only the glucose concentration or only the hematocrit may be derived as target variables. The target variable Y may be a scalar or a vector or a matrix.

The target value may be different from the at least one analyte concentration. Alternatively, the target value may be the at least one analyte concentration or may include the at least one analyte concentration. For example, the target value may be a different physical and/or chemical quantity as the at least one analyte concentration or the target value may be the same physical or chemical quantity as the at least one analyte concentration.

Likewise, the at least one analyte concentration may be an arbitrary concentration. For example, the at least one analyte concentration may be a glucose concentration, especially a blood glucose concentration. A typical unit of the blood glucose concentration may be mmol/l or mg/dl. More than one target variable Y may be combined to a vector.

In step d), in addition to the at least one target variable Y, at least one electrochemical measurement value may be used for determining the at least one analyte concentration. The electrochemical measurement value may be determined by using at least one electrochemical measurement. The electrochemical measurement may be a measurement being able to generate electrochemical measurement values. For example, the measurement curve as described above may be an electrochemical measurement curve. The electrochemical measurement curve may include electrochemical measurement values. In some instances, the electrochemical measurement may be an amperometric measurement. The electrochemical measurement may include at least one measurement using at least one electrode. Alternatively, the electrochemical measurement may be a measurement using at least one electrical current measurement and/or at least one electrical voltage measurement and/or at least one impedance measurement. As such, the electrochemical measurement value may be an electrical current and/or an electrical voltage or an impedance, where the electrical current and/or the electrical voltage and/or the impedance may correlate with the at last one analyte concentration such as a glucose concentration.

For example, the electric current may be proportional to the glucose concentration. The electrochemical measurement value may be a raw value as discussed above. The electrochemical measurement value may be corrected by using the target variable Y, especially for generating a corrected analyte concentration such as, for example, a corrected glucose concentration. The at least one analyte concentration may be determined by the electrochemical measurement. The optical measurement curve may only be used for a correction, such as a calculated correction, of the electrochemical measurement, especially of the electrochemical measurement value. The correction may include the correction algorithm as described above.

By using the electrochemical measurement value, an approximated value of the at least one analyte concentration in the body fluid sample may be determined. The approximated value of the at least one analyte concentration in the sample may be a raw value as discussed above. Alternatively, the target value Y may be used for correcting the approximated value. In this manner, the target value Y may include an influence of hematocrit and/or a hematocrit concentration on the at least one analyte concentration (e.g., a glucose concentration).

In addition to steps a)-d), the methods disclosed herein may further include at least one calibration step. In the calibration step, a plurality of calibration measurement curves may be generated by acquiring measurement curves of a plurality of calibration fluids, such as optical measurement curves of a plurality of calibration fluids, with the respective known target variables Y. The characteristic values may be determined for each calibration measurement curve. For example, an equation system including the coefficients of one or more of equations (4)-(6) above may be solved. Thereby, numeric values for the coefficients may be determined. The calibration fluid may be a fluid having a known target variable, such as a known concentration of the at least one analyte, especially a concentration of the analyte determined by a reliable reference method. The calibration fluid may be a fluid most preferably having a known analyte concentration (e.g. having a known glucose concentration). Thus, the calibration fluid may include a glucose solution having a known glucose concentration, such as a glucose concentration of about 0-500 mg/dl. The calibration measurement curve may be a measurement curve being acquired by using a calibration fluid and/or the calibration measurement curve may be acquired under known conditions, such that at least one target variable Y may be known. Thus, in case the target variable Y may refer to the calibration fluid, the target variable Y may be known via the calibration fluid itself. In case the target variable Y may refer to the measurement conditions, such as a temperature and/or specific properties of the test substance used for the measurement and/or one of the state variables, the target variable Y may be known from the circumstances of the measurement.

Methods incorporating the inventive concept also can include detecting an analyte in a body fluid sample. The analyte, the sample and the body fluid may be defined as discussed above.

Briefly, the methods can include the following steps:

Step i): providing at least one measurement curve, where the measurement curve contains a plurality of measurement values recorded by monitoring a time development of at least one measurement value indicating a progress of a detection reaction of at least one test substance and a body fluid sample. The measurement values contained in a measurement curve are acquired at differing points in time. The detection reaction is known to be influenced by a set of state variables. Each state variable characterizes at least one of a state of the body fluid sample and a condition of the detection reaction.

Step ii): determining at least one target variable Y and/or at least one estimate value for at least one target variable Y by using a first time interval $t_1$ of the measurement curve, where $0 \leq t_1 \leq x \cdot s$, and where the target variable Y is different from at least one analyte concentration.

Step iii): determining the at least one analyte concentration by using the at least one target variable.

For further optional details of these methods, as well as for definitions of the terms used in connection with these methods, reference may be made to the first methods described above.

Here, however, the measurement curve does not necessarily have to be an optical measurement curve, even though this option still exists. Thus, other types of measurement curves containing a plurality of measurement values recording by monitoring a time development of at least one measurement value indicating a progress of a detection reaction of at least one test substance and the body fluid sample. The detection reaction may be adapted to change at least one measurable property of at least one test substance itself and/or the body fluid sample. The at least one measurable property does not necessarily have to be an optical property and, besides the option of being an optical property, may be or may include one or more of an electrical property and/or a chemical property. Thus, for example, the measurement values in the second methods may be or may include electrical or electrochemical measurement values.

Consequently, besides the option of using a test substance that changes at least one optical property due to the detection reaction, other types of test substances may be used additionally or alternatively, such as at least one test substance that changes at least one electrochemical property and/or at least one electrical property due to the detection reaction. Thus, for example, in the first methods disclosed above, at least one test element having at least one optical test substance may be used, whereas, in the second methods disclosed here and/or in the third methods disclosed in further detail below, at least one test element having at least one of an optical test substance and an electrochemical test substance may be used. As such, the measurement curves used and/or evaluated in the second methods and/or the third methods may be selected from optical measurement curves and electrochemical measurement curves. Other options are feasible. Furthermore, the measurement values in the second methods and/or the third methods may be selected from optical measurement values and electrochemical measurement values; however, other options are feasible.

Besides the fact that the measurement curve does not necessarily have to be an optical measurement curve, the terms used in the second methods may be defined as the identical terms as in the first methods above. The first time interval $t_1$ may be a time interval as described above. The time interval $t_1$ may include at least two measurement values. x may be smaller or equal to 2, notably x may be smaller or equal to 0.2.

The second methods also may include the following steps:

Step iv): providing a set of at least two different evaluation rules, where each evaluation rule may be adapted to derive a characteristic value from the measurement curve, thereby deriving a set of characteristic values $X=\{X_i\}_{i=1 \ldots N}$ from the measurement curve. The set of characteristic values includes at least one first characteristic value being derived from the measurement curve by using at least one first evaluation rule from the set of evaluation rules and at least one second characteristic value being derived from the measurement curve by using at least one second evaluation rule from the set of evaluation rules. The second evaluation rule is different from the first evaluation rule.

In some instances, step iv) may be executed by using at least one computer.

Step v): performing at least one multivariate analysis of the at least one first characteristic value and the at least one second characteristic value by using at least one predetermined multivariate evaluation algorithm, where the multivariate evaluation algorithm is an algorithm adapted to derive at least one result from at least two variables. The at least one first characteristic value and the at least one second characteristic value are used as the at least two variables, thereby deriving the at least one estimate value for at least one target variable Y of the state variables. In some instances, the measurement curve may be an optical measurement curve, especially an optical measurement curve as described above.

The measurement values contained in the measurement curve may be acquired at identical measuring conditions. As used herein, "identical measuring conditions" means a state of the sample during the measurement. The sample may be not influenced be an application of an electrical voltage and/or an electrical current (e.g., by using DC and/or AC pulses). The measurement curve may include or may exclusively be measurement values acquired at identical measuring conditions. Identical measuring conditions may not be given if an alternating current and/or an alternating voltage is applied on the sample. In some instances, measurement values measured in step i) may be acquired at identical measuring conditions.

The first evaluation rule may be transformed, or at least may be transformable, into the second evaluation rule by a time transformation.

Alternatively, the first evaluation rule may not be transformed, or at least may not be transformable, into the second evaluation rule by a time transformation.

Methods incorporating the inventive concept also can include characterizing a body fluid sample. As used herein, "characterizing" means a qualitative and/or quantitative determination of at least one property of the body fluid sample or a part thereof. The analyte, the sample and the body fluid may be defined as discussed above.

Briefly, the methods can include the following steps:

Step A): bringing the body fluid sample into contact with at least one test substance, thereby initiating a detection reaction of the test substance and the body fluid sample, where the detection reaction is known to be influenced by a set of state variables. Each state variable characterizes at least one of a state of the body fluid sample and a condition of the detection reaction.

Step B): monitoring a time development of at least one measurement value indicating a progress of the detection reaction, thereby recording an optical measurement curve containing a plurality of the measurement values acquired at different points in time.

Step C): evaluating the optical measurement curve by fully or partially using one of the methods as described herein.

For further optional details of the third methods, as well as for definitions of the terms used in the third methods, reference may be made to the first or second methods disclosed hereinabove.

Here, in method step C), one, more than one or all of the method steps of the first and/or second methods may be performed, with the exemption that the measurement curve not necessarily has to be an optical measurement curve. Thus, other types of measurement curves containing a plurality of measurement values recording by monitoring a time development of at least one measurement value indicating a progress of a detection reaction of at least one test substance and the body fluid sample. The detection reaction may be adapted to change at least one measurable property of at least one of the test substance itself and/or the body fluid sample. The at least one measurable property not necessarily has to be an optical property and, besides the option of being an optical property, may be or may include one or more of an electrical property and/or a chemical property. For example, the measurement values of the second methods may be or may include electrical or electrochemical measurement values.

Likewise, one or more or even all of method steps a)-d) of the first methods may be performed, with the exemption that, as outlined above, the measurement curve not necessarily is an optical measurement curve. For example, the measurement curve may be an electrochemical measurement curve. For further optional details, reference may be made to first methods disclosed hereinabove and below. Additionally or alternatively, one, more than one or even all of method steps i), ii) and iii) of the second methods may be performed.

Computer Programs and Data Carrier Structures

Computer programs also are disclosed that incorporate the inventive concept. Such computer programs can include computer-executable instructions for performing one or more of the methods as disclosed herein when the program is executed on a computer or a computer network. In connection with the methods, at least the steps a)-c) and/or the step b3) may be executed by using the computer program. Additionally or alternatively, one, more than one, or even all of method steps i), ii), iii), iv) and v) may be executed by using the computer program. Again, additionally or alternatively, one or both of method steps B) and C) may be executed by using the computer program.

Specifically, the computer program may be stored on a computer-readable data carrier.

Computer program products having program code means also are disclosed that incorporate the inventive concept. The computer program products can perform the methods as disclosed herein when the programs are executed on a computer or computer network. Specifically, program code means may be stored on a computer-readable data carrier.

Data carriers having a data structure stored thereon also are disclosed that incorporate the inventive concept. The structures, which, after loading into a computer or computer network, such as into a working memory or main memory of the computer or computer network, may execute the methods as disclosed herein.

Computer program products with program code means stored on a machine-readable carrier also are disclosed that incorporate the inventive concept. The products with program codes can perform the methods disclosed herein when the program is executed on a computer or computer network. As used herein, "a computer program product" means a program as a tradable product. The product may generally exist in an arbitrary format, such as in a paper format, or on a computer-readable data carrier. Specifically, the computer program product may be distributed over a data network.

Modulated data signals containing instructions readable by a computer system or computer network also are disclosed that incorporate the inventive concept. The data signals can perform the methods as disclosed herein.

With respect to such computer-implemented aspects of the disclosure, one or more of the method steps or even all of the method steps of the methods disclosed herein may be performed by using a computer or computer network. Thus, generally, any of the method steps including provision and/or manipulation of data may be performed by using a computer or a computer network. Generally, these method steps may include any of the method steps, typically except for method steps requiring manual work, such as providing the samples and/or certain aspects of performing the actual measurements.

These aspects further include:

A computer or computer network including at least one processor, where the processor is adapted to perform at least one of the methods disclosed herein;

A computer loadable data structure adapted to perform at least one of the methods disclosed herein while the data structure is being executed on a computer;

A computer program adapted to perform at least one of the disclosed herein while the program is being executed on a computer;

A computer program including program means for performing at least one of the methods described herein while the computer program is being executed on a computer or on a computer network;

A computer program including program means as described above, where the program means are stored on a storage medium readable to a computer;

A storage medium, where a data structure is stored on the storage medium and where the data structure is adapted to perform at least one of the methods disclosed herein after having been loaded into a main and/or working storage of a computer or of a computer network; and A computer program product having program code means, where the program code means can be stored or are stored on a storage medium, for performing at least one of the methods disclosed herein, if the program code means are executed on a computer or on a computer network.

Devices

Evaluation devices also are disclosed for evaluating an optical measurement curve for analyzing at least one body fluid sample and incorporate the inventive concept. Such devices can include at least one evaluation unit adapted to perform at least one of the methods for evaluating a measurement as disclosed herein. The evaluation device may be an evaluation device being able to evaluate the optical measurement curve.

Sample analysis devices also are disclosed for characterizing a sample of a body fluid and incorporate the inventive concept. Such devices include at least one measuring unit for measuring a detection reaction of at least one test substance and at least one body fluid sample. The detection reaction is known to be influenced by a set of state variables, where each state variable characterizes at least one of a state of the body fluid sample and a condition of the detection reaction. The measuring unit further is adapted for monitoring a time development of at least one measurement value indicating a progress of the detection reaction, thereby recording an optical measurement curve containing a plurality of the measurement values acquired at different points in time.

In addition, the sample analysis devices may include at least one evaluation device as described above.

Furthermore, the sample analysis devices may include at least one test element such as at least one test strip. The test element may contain the at least one test substance adapted to perform the detection reaction.

The sample analysis devices therefore may be adapted such that the body fluid sample can be applied to the test element. The test element may be a part of the sample analysis device being able to contain the test substance and being able to perform the detection reaction. The test element may be arranged such that the optical measurement curve and/or the measurement curve may be generated. The sample analysis devices may be arranged to get the optical measurement curve and/or the electrochemical measurement curve. The sample analysis devices may be embodied as a hand-held device. As used herein, "hand-held device" means that the sample analysis devices may be used by a single user and may be carried in a hand.

Moreover, the sample analysis devices may include at least one detector. The detector may be or may include at least one detector array such as, for example, a detector offering a spatial resolution. Alternatively, the detector may be a single detector or may include only one detection segment (e.g., a detector having no spatial resolution).

In FIG. 1, an embodiment of an analysis device 110 is shown for characterizing a body fluid sample. The device 110, such as a sample analysis device, includes at least one measuring unit 112 for measuring a detection reaction of at least one test substance and at least one body fluid sample. The detection reaction is known to be influenced by a set of state variables. Each state variable characterizes at least one of a state of the body fluid sample and/or a condition of the detection reaction. The measuring unit 112 further is adapted for monitoring a time development of at least one measurement value indicating a progress of the detection reaction, thereby recording an optical measurement curve and/or a measurement curve containing a plurality of the measurement values acquired at different points in time.

The device 110 further can include at least one evaluation device 114. The evaluation device 114 may be an evaluation device for evaluating an optical measurement curve and/or a measurement curve for analyzing at least one sample of a body fluid. The evaluation device 114 can include at least one evaluation unit 116 adapted to perform a method as disclosed herein.

The device 110 also may include at least one test element 118, especially at least one test strip 120. The test element 118 may contain the at least one test substance adapted to perform the detection reaction. The device 110 may be adapted such that the body fluid sample is applicable to the test element 118.

Additionally or alternatively, the test element 118, especially the test strip 120, may be reversibly attached to the sample analysis device 110. The test element 118 may alternatively be not a part of the device 110. The test element 118 and/or the test strip 120 may be able to be inserted into the sample analysis device 110 after attaching/applying the body fluid sample on the test element 118.

The device 110 may be embodied as a hand-held device 122. In this manner, the device 110 also may include at least one monitor 124 (e.g., at least one touchscreen and/or at least one screen and/or at least one display). The monitor 124 may be adapted to display a concentration of the at least one analyte and/or at least one estimate value for the at least one target variable. The device 110 further may include at least one input panel 126. The input panel 126 may be designed to act as an interface between a user and the device 110. The input panel 126 may include at least one key and/or at least one keyboard and/or at least one knob and/or at least one touchscreen and/or at least one touchscreen pad. In some instances, the monitor 124 and the input panel 126 may be separated from each other. In other instances, the input panel 126 may be integrated in the monitor 124 (e.g., as in a touchscreen panel).

The measuring unit 112 may include at least one light source 128. The light source 128 may include at least one light emitting diode (LED) and/or at least one laser and/or at least one lamp. The measuring unit 112 also may include at least one detector 130. The detector 130 may be a device being able to detect light being emitted by the sample and/or being reflected by the sample and/or by the test element 118 and/or being emitted by the light source 128. The detector 130 may be able to detect the remission (e.g., a reflection and/or a scattering of the light emitted by the light source 128 and/or by the test element 118 and/or by the sample 110 and/or by the analyte). The detector 130 alternatively or additionally may be able to detect a fluorescence signal emitted by the test element 118 and/or by the sample and/or by the analyte.

The sample analysis device 110, especially the measuring unit 112, may include different components for doing spectroscopy of the sample and/or of the analyte.

The measuring unit 112 further may include at least one lance and/or at least one filter and/or at least one mirror and/or at least one wavemeter.

The detector 130 may include at least one photodiode (e.g., an avalanche photodiode), and/or at least one CCD chip and/or at least one camera and/or at least one wavemeter and/or at least one frequency comb and/or at least one spectroscopy cell. The detector 130 may be able to detect light by generating at least one signal, preferably be generating the measurement curve and/or the optical measurement curve. The signal may be detected in dependence of a time t and/or may be integrated over a certain time period.

The sample analysis device 110 also may include at least one computer 132 and/or at least one computer network 134. The computer 132 and/or the computer network 134 may be integrated in the evaluation unit 116. The computer 132 and/or the computer network 134 may also be at least partially separated from the sample analysis device 110. The computer 132 and/or the computer network 134 may be able to be connected to the sample analysis device 110 by at least one interface (e.g., by at least one USB connection).

The computer 132 and/or the computer network 134 and/or the sample analysis device 110 may be adapted to execute at least one computer program. The computer program includes computer-executable instructions for performing at least one of the methods as disclosed herein when the program is executed on the computer 132 and/or on the computer network 134.

The sample analysis device 110 may include at least one photometric glucose element (e.g., the test strip 120). The sample analysis device 110 may be an Accu-Chek® Active system by Roche Diagnostics Deutschland GmbH. The following embodiments may refer to photometric glucose strips and/or the Accu-Chek® Active system, but the methods, as well as the computer programs and/or the evaluation devices and/or the sample analysis devices 110 may alternatively be assigned to a plurality of different systems, especially systems in which at least one analyte concentration should be determined and a accuracy of reading of a measured signal may depend on additional properties of the sample and/or of the measurement and/or of other circumstances (e.g., of at least one state variable).

The methods disclosed herein also may be combined with electrochemical measurements of an analyte in a body fluid sample (e.g., referring to glucose test elements and/or absorption kinetics in lab analysis systems).

Another method of detecting an analyte in a body fluid sample is disclosed herein and includes the following steps:

i). providing at least one measurement curve, where the measurement curve contains a plurality of measurement values recorded by monitoring a time development of at least one measurement value indicating a progress of a detection reaction of at least one test substance and the sample of a body fluid, where the measurement values contained in the measurement curve are acquired at differing points in time 136, and where the detection reaction is known to be influenced by a set of state variables, each state variable characterizing at least one of a state of the body fluid sample and a condition of the detection reaction;

ii). determining at least one target variable and/or at least one estimate value for at least one Y by using a first time interval $t_1$ of the measurement curve, where $0 \leq t_1 \leq x$, and where the target variable Y is different from a concentration of the at least one analyte; and iii). determining at least one analyte concentration by using the at least one target variable.

The methods further may include the following step:

iv). providing a set of at least two different evaluation rules, each evaluation rule being adapted to derive a characteristic value 138 from the measurement curve, thereby deriving a set of characteristic values $X=\{X_i\}_{i=1\ldots N}$ from the measurement curve, the set of characteristic values 138 including at least one first characteristic value 138 being derived from the measurement curve by using at least one first evaluation rule from the set of evaluation rules and at least one second characteristic value 138 being derived from the measurement curve by using at least one second evaluation rule from the set of evaluation rules, the second evaluation rule being different from the first evaluation rule, preferably by using a computer 132.

The methods further may include the following step:

v). performing at least one multivariate analysis of the at least one first characteristic value 138 and the at least one second characteristic value 138 by using at least one predetermined multivariate evaluation algorithm, the multivariate evaluation algorithm being an algorithm adapted to derive at least one result from at least two variables, where the at least one first characteristic value 138 and the at least one second characteristic value 138 are used as the at least two variables, thereby deriving the at least one estimate value for at least one target variable Y of the state variables.

The measurement curve may be an optical measurement curve. The measurement values contained in the optical measurement curve may be acquired at identical measuring conditions. The first evaluation rule may not be transformed, or at least may not be transformable, into the second evaluation rule by a time transformation.

FIGS. 2A to 7 show exemplary methods of detecting an analyte in a body fluid sample.

In connection therewith, a method of detecting an analyte in a body fluid sample includes the following steps:

a). providing at least one optical measurement curve containing a plurality of measurement values recorded by monitoring a time development of at least one measurement value indicating a progress of a detection reaction of at least one test substance and the sample of a body fluid. The measurement values contained in the optical measurement curve are acquired at different points in time 136. The detection reaction is known to be influenced by a set of state variables, where each state variable characterizes at least one of a state of the body fluid sample and a condition of the detection reaction;

b). providing a set of at least two different evaluation rules, where each evaluation rule is adapted to derive a characteristic value 138 from the optical measurement curve, thereby deriving a set of characteristic values $X=\{X_i\}_{i=1\ldots N}$ from the optical measurement curve The set of characteristic values 138 includes at least one first characteristic value 138 being derived from the optical measurement curve by using at least one first evaluation rule from the set of evaluation rules and at least one second characteristic value 138 being derived from the optical measurement curve by using at least one second evaluation rule from the set of evaluation rules. The second evaluation rule is different from the first evaluation rule;

c) performing at least one multivariate analysis of the at least one first characteristic value 138 and the at least one second characteristic value 138 by using at least one predetermined multivariate evaluation algorithm. The multivariate evaluation algorithm is an algorithm adapted to derive at least one result from at least two variables. The at least one first characteristic value 138 and the at least one second characteristic value 138 are used as the at least two variables, thereby deriving at least one estimate value for at least one target variable Y of the state variables; and d) determining at least one analyte concentration by using the at least one target variable.

For an evaluation, especially not only one characteristic value 138 (e.g. a parameter, like an end value and/or a derivative and/or something similar) is used but a plurality of parameters (e.g., a plurality of characteristic values 138, especially at least two characteristic values 138) of a kinetic curve are used. The methods disclosed herein may not exclusively use a univariate analysis with only one parameter (e.g., only one characteristic value 138), but a multivariate analysis with more parameters, especially with at least two characteristic values 138.

This may be the reason why using the predetermined multivariate evaluation algorithm may also be called multivariate analysis. Methods of executing the multivariate analysis and/or multivariate evaluation algorithms are described, for example, in Martens & Næs (1998) supra, and/or Henrion & Henrion (1995) supra.

Although, the following embodiments are predominantly described for analyzing kinetic curves of blood glucose measurements, the methods herein may alternatively be used in a wider context of analyzing data, especially but not exclusively, of time dependent data. The optical measurement curve may be a measurement curve changing during a fermentation for analyzing the fermentation by using at least one method as disclosed herein for making production processes more stable.

The use of the methods herein may be especially advantageous by using periodic and/or similar developing optical measurement curves. The methods therefore may be used for avoiding an influence of a state variable such as, for example, hematocrit and/or a temperature on a detection of the analyte in the body fluid sample. At least one of the characteristic values 138 may not just be a measurement value, but a characteristic value 138. At least one of the characteristic values 138 may be different from a simple measurement value. The points in time 136 may be distributed over about 0 seconds to about 5 minutes, about 0 seconds to about 101 seconds, about 0 seconds to about 30 seconds, or even about 3 seconds to about 6 seconds.

The methods herein may not be part of a closed loop and/or may not be part of a closed loop.

In the methods herein, at least one test strip 120 may be observed. In some instances, the analyte in the body fluid sample may be detected only once. For example, only one body fluid sample may be taken from the body once the method is performed. Thus, the optical measurement curve may be a single measurement on the test element 118 (e.g., the test strip 120) and not a periodic signal.

Alternatively, the methods herein may be performed periodically on different body fluid samples and/or may be part of a closed loop.

A relationship between a signal (e.g., the optical measurement curve and/or the measurement curve, especially at least one integration of at least a part of the optical measurement curve) may be inversed proportional to the concentration of glucose. For example, a high glucose concentration may result in a smaller signal. The relationship between the glucose concentration and the signal may be provided by a calibration curve (e.g., for optical sample analysis devices 110). The calibration curve and/or the relationship between the glucose concentration and the signal may include at least one exponential function.

The methods herein may provide a simultaneous correction of at least two error sources, especially of all error sources influencing the analyte detection. The simultaneous correction may be performed without knowledge of connections and/or correlations and/or relationships between individual error sources (e.g., between individual state variables). The methods herein may perform a simultaneous correction, where an individual correction term may not have to be known and/or may not have to be used therein.

The methods herein may include a simultaneous correction, where a simultaneous correction may be defined as an opposite of a sequential correction. In a sequential correction, error sources may be corrected successively (e.g., one error source after another). In the methods, no successive methods may be performed. In the methods, each step only may be performed once, especially step d) may only be performed once.

The state variables may be selected from: a composition of a body fluid sample, especially a content of at least one component of the body fluid sample such as at least one analyte concentration; a content of at least one particulate component of the body fluid sample, especially a hematocrit; a temperature of the body fluid sample; a humidity of an ambient atmosphere surrounding the body fluid sample; a storage time of the test substance; a storage history (e.g., of the test element 118, which may influence the test signal). The state variables, such as the storage history, may change at least one of the measurement values and/or at least one prominent point of the optical measurement curve (e.g., at least one minimum such as a local minimum, and/or at least one maximum and/or at least one turning point and/or at least one other characteristic point and/or at least one value of at least one derivative of the optical measurement curve and/or the time of their appearances). A particulate component may be acetylsalicylic acid and/or citric acid and/or maltose and/or xylose.

The methods herein may be able to suppress interferences caused by the state variables or even may be able to compensate at least a part of the interferences caused by the state variables. The methods herein may give the opportunity to determine a state of a reagent kit (e.g., of a test strip 120 in terms of at least one activity of an enzyme such as glucose oxidase and/or glucose dehydrogenase and/or glucose deoxyreductase and/or similar components).

The methods and devices herein may be used in detecting analyte concentrations, especially in detections of analyte concentrations wherein an accuracy of reading out of the measured signal may be influenced by using methods and devices known from prior art by other properties besides the analytes concentrations on properties of the sample and/or of the measurement.

The methods herein, especially when using multivariate analysis, not only may be limited to optical detection methods but also may be applicable in systems being able to execute a different unperturbed measurement.

The methods herein also may be used in electrochemical detection methods and/or may include electrochemical detection methods. In a multivariate analysis, not only one parameter (e.g., not only one characteristic value 138) is used but also a plurality of parameters (e.g., a plurality of characteristic values 138) is used. The multivariate analysis may deviate from a univariate analysis.

The influences of the state variables, like temperature and/or hematocrit, may influence the optical measurement curve (e.g., the kinetic curve) in such a way that these interference factors and/or state variables may be able to be determined by the at least two characteristic values 138. The two characteristic values 138 may differ from each other and/or may be independent parameters. The set of characteristic values 138, especially the two characteristic values 138, may be determined out of only one optical measurement curve (e.g. out of only one kinetic curve). The influences of the state variables may be quantified by the at least two characteristic values 138. The two characteristic values 138 may include the first characteristic value 138 and the second characteristic value 138.

In the methods herein, besides the detection of at least one analyte concentration at least one additional state variable (e.g., the temperature and/or the hematocrit and/or another state variable) may be determined by, for example, evaluating one single optical measurement curve (e.g., one single kinetic curve).

The first evaluation rule may not be transformed, or at least not be transformable, into the second evaluation rule by a time transformation. The first characteristic value 138 may be determined by using a first time interval of the optical measurement curve. The second characteristic value 138 may be determined by using a second time interval of the optical measurement curve. The first time interval of the optical measurement curve may be different from the second time interval of the optical measurement curve. The target value may be different from the at least one analyte concentration.

The at least two evaluation rules may be adapted to derive the characteristic values 138 from at least two derivatives of the optical measurement curve. The characteristic values 138 may be derived by using at least two derivatives of the optical measurement curve. At least one of the derivatives of the optical measurement curve not only may be used for determining a criterion (e.g., an end point value). At least one quantitative value of the derivatives of the optical measurement curve may be used directly for deriving at least one of the characteristic values 138. For example, the numerical value of the first derivative of the optical measurement curve of a remission kinetic curve may be included in the evaluation. By evaluating only one optical measurement curve (e.g., only one kinetic curve), at least one hematocrit value and/or at least one analyte concentration and/or at least one temperature and/or at least one another state variable may be able to be determined, especially quantitatively. Alternatively, the two evaluation rules may differ from each other by applying two different components related to the algorithm, such as two different thresholds or two different change rates below a predetermined threshold.

The at least two derivatives may be derivatives including at least two derivatives of different order. The order of the derivatives may range from 0 to n, where n is a natural number.

The derivatives may be generated by using at least one filtering algorithm, such as a Savitzky-Golay filtering algorithm. The Savitzky-Golay filter is a filter known from data analysis. The filtering algorithm may be a filter and may range up to the order.

During using the filtering algorithm, 11 neighboring measurement values or data points in, for example, a distance of 0.1 seconds may be examined.

Additionally or alternatively, at least one spline function may be fitted, preferably segmentally, to the optical measurement curve and/or to the measurement curve (e.g., to the kinetic curve). A spline function may be a sufficiently smooth polynomial function. The spline function may be piecewise-defined. The spline function may possess a high degree of smoothness at places where polynomial pieces may connect. These places may be called knots. In the methods herein, at least one polynomial interpolation may be used. The knots may have a distance of about 0.1 seconds. Additionally or alternatively, knots having a varying distance may be used, such as a small distance in regions in which a high alteration rate of the curves is encountered and a higher distance in regions in which a low alteration rate of the curves is encountered. Thus, the density of the knots may be adapted to the degree of changes or alterations in the curves.

Significant changes of the optical measurement curve often may take place shortly after bringing the body fluid sample into contact with the at least one test substance (e.g., with a test element 118, especially with a test strip 120).

A functional dependency of the optical measurement curve, e.g. of a development of the remission in time on at least one state variable, e.g. on a hematocrit value, may be seen as a perturbation of the detection of the analyte in the sample, preferably of determining the at least one analyte concentration (e.g., the determining of glucose), but on the other hand, information about at least one state value (e.g., about a hematocrit concentration) may be included in the measurement curve and/or in the optical measurement curve (e.g., in the kinetic curve).

The optical measurement curves (e.g., measured kinetic curves) and/or the at least two derivatives of the optical measurement curve (e.g., the first derivative and/or the second derivative and/or the third derivative) may be divided in time intervals starting with bringing the body fluid sample into contact with the at least one test substance at t=0.

As essential changes often may happen shortly after bringing the body fluid sample into contact with the at least one test substance such as the test element 118 and/or the test strip 120, it may be advantageous to use time intervals with different length instead of using equidistant time intervals.

Additionally or alternatively, the time intervals at least partially may be equidistant. For example, the time intervals may be short shortly after bringing the body fluid sample into contact with the at least one test substance, where the short time interval may last about 1 ms to about 2 s, about 10 ms to about 1 s, or even about 100 ms. For later times, longer time intervals may be useful such as about 1 s to about 5 s, about 1.5 s to about 2.5 s, or even about 2 s. For example, an optical measurement curve of about 30 s may be divided in 23 time intervals, where the length of the time intervals may increase proportional to the square root of the time.

Additionally or alternatively, the optical measurement curve may be divided in different parts of the optical measurement curve (e.g., in different time intervals), where different analysis methods may be applied to the parts of the optical measurement curve (e.g., different evaluation rules). The evaluation rule may include determining at least one slope for a first part of the optical measurement curve and/or determining at least one second derivative for at least one second part of the optical measurement curve or something similar.

The set of characteristic values 138 may contain 2-20 characteristic values 138, especially 3-10 characteristic values 138. The target variable Y may include at least one analyte concentration in the body fluid sample such as a glucose concentration.

In step d), in addition to the at least one target variable Y, at least one electrochemical measurement value may be used for determining the analyte concentration. The electrochemical measurement value may be determined by using at least one electrochemical measurement. By using the electrochemical measurement value, an approximated value of the at least one analyte concentration in the body fluid sample may be determined. The target value Y may be used for correcting the approximated value.

The predetermined multivariate evaluation algorithm may i at least one polynomial algorithm selected from:

$$Y = A \cdot X, \quad (1);$$

$$Y = X^T \cdot A \cdot X, \quad (2); \text{ and}$$

$$Y = X^T \cdot (X^T \cdot A \cdot X), \quad (3),$$

A may be a one-dimensional, a two-dimensional or a three-dimensional evaluation tensor. In some instances, A may be a symmetric tensor. For example, A may be a 3×3 tensor. X and/or Y may be vectors or matrixes. In some instances, Y is a matrix or a vector that includes different target variables; and X can be a matrix or a vector that includes at least two different characteristic values. Other polynomial algorithms also may be used.

Alternatively, the predetermined multivariate evaluation algorithm may include at least one algorithm selected from:

$$Y = \Sigma_i a_i \cdot X_i, \quad (4);$$

$$Y = \Sigma_i a_i \cdot X_i + \Sigma_{i,j} a_{ij} \cdot X_i \cdot X_j, \quad (5); \text{ and}$$

$$Y = \Sigma_i a_i \cdot X_i + \Sigma_{i,j} a_{ij} \cdot X_i \cdot X_j + \Sigma_{i,j,k} a_{ijk} \cdot X_i \cdot X_j \cdot X_k, \quad (6).$$

$a_i$, $a_{ij}$, $a_{ijk}$ may be predetermined coefficients. i, j and k may be, mutually independent, integers from 1 to N.

The method also may include at least one calibration step. Formula (5) may show that the use of squared terms already may be sufficient. Formula (6) may show that cross terms between the characteristic values 138 (e.g., products of two characteristic values 138) may be important. It may be convenient to use the characteristic values $X_i$ (e.g., input parameters) not only in linear combinations, similar to the partial least squares (PLS) method, but additionally or alternatively also use products of the characteristic values 138 (e.g., of the input parameters) among themselves and/or squares of the characteristic values 138 (e.g., of an input parameters) expressed by cross terms. In other words, it may be advantageous to use formula (5) instead of formula (4). Y may be the predicted glucose values.

The characteristic value 138 may be an end value. The end value as a single characteristic value 138 (e.g., as single parameter) may be used in the PLS and/or may be used in a squared term as at least the square of the end value. In such a case, the multivariate analysis (e.g., the multivariate data analysis) may only include two characteristic values 138, especially two input values (e.g., $X_{EV}$=EV (end value) and $X_{EV}^2$=EV$^2$, with respective coefficients $a_{EV}$ and $a_{EVEV}$. Such a step already may decrease a median of a prediction error from about 6.3 to about 4.8.

The methods further may include at least one calibration step. In the calibration step, a plurality of calibration measurement curves may be generated by acquiring measurement curves, especially optical measurement curves, of a plurality of calibration fluids with the respective known target variables Y. The characteristic values 138 may be determined for each calibration measurement curve. An equation system including the coefficients of one or more of Equations (4)-(6) may be solved, thereby determining numeric values for the coefficients.

At least one influence of at least one state variable (e.g., of the hematocrit) may be measured before the calibration for taking the influence into account in the calibration step (e.g., in a multivariate calibration). In the calibration step, dependencies on the state variables (e.g., on hematocrit) may be taken into account. A computation and/or application of at least one derivative by using the Savitzky-Golay filter may take place inside the evaluation device 114. In the methods herein, terms of higher order with a plurality of sectors may be taken into account.

In step b), the evaluation rules may be adapted such that the characteristic values 138 may be linearly independent, thereby generating unique solutions for the numeric values of the coefficients.

The at least one multivariate evaluation algorithm may include at least one algorithm selected from: a partial least squares regression algorithm (PLSR); a principal component regression algorithm (PCR) a support vector machine algorithm (SVM); an artificial neuronal network algorithm (ANN); and/or a genetic algorithm (GA). The characteristic values 138 may be independent (e.g., co-linear) in a mathematical sense. The characteristic values 138 may be extracted out of one and the same measurement curve, especially out of one and the same optical measurement curve (e.g., out of one and the same kinetic curve).

The body fluid may be selected from blood, interstitial fluid, urine, plasma, serum and saliva. The monitoring of the time development of the at least one measurement value indicating the progress of the detection reaction may be adapted to be an impact-free monitoring of the detection reaction without influencing the detection reaction. An impact-free monitoring may be a measurement, where no, or with no significant, impact on the measurement procedure may happen during the actual generation of the measurement signals, especially of the optical measurement curve.

In the methods herein, at least one of the two different evaluation rules may be selected from:

a. using a specific measurement value of the optical measurement curve or a derivative of the optical measurement curve at a predetermined point in time as the characteristic value 138;

b. using a mean value of the optical measurement curve or a derivative of the optical measurement curve over a predetermined period of time as the characteristic value 138, especially using one or more specific criteria, particularly using one or more specific conditions, which may include at least one end value criterion, especially a change rate below a predetermined threshold value;

c. using a characteristic point in time of the optical measurement curve or of a derivative of the optical measurement curve as the characteristic value 138, especially a characteristic point in time at which one or more of the following occur: a maximum of the optical measurement curve or of a derivative of the optical measurement curve; a minimum of the optical measurement curve or of a derivative of the optical measurement curve; and/or an inflection point of the optical measurement curve or of a derivative of the optical measurement curve;

d. using a characteristic parameter of the optical measurement curve or of a derivative of the optical measurement curve as the characteristic value 138, especially a characteristic parameter at one of: a maximum of the optical measurement curve or of a derivative of the optical measurement curve; a minimum of the optical measurement curve or of a derivative of the optical measurement curve; and/or an inflection point of the optical measurement curve or of a derivative of the optical measurement curve;

e. using a fit parameter derived by at least one fitting process as the characteristic value 138. The fitting process may imply a fitting of at least one predetermined fit curve to at least a section of the optical measurement curve or of a derivative of the optical measurement curve; and f. using at least one value derived from a phase plot as shown, for example, in FIGS. 6A and/or 6B, of at least two derivatives of different order of the optical measurement curve as the characteristic value 138, where the phase plot may include at least one phase space curve, where the value derived from the phase plot preferably may be selected from: a position of a center of the phase space curve; a length of the phase space curve; a phase space volume; a phase space area; a point with a maximal distance to the center of the phase space curve; and/or a mean squared distance from the origin of the phase space.

The phase plot may be used for detecting the analyte in the body fluid sample, especially the phase plot may be used for determining the glucose concentration. The phase plot may be used for a calculation of at least one parameter, especially for a calculation of the characteristic values 138, out of the optical measurement curve for detecting the analyte in the body fluid sample, especially for calculating glucose concentration. The analyte concentration (e.g., the glucose concentration) may be the result of the phase plot. The phase plot may be an input quantity for determining the analyte concentration, especially for determining glucose concentration.

At least two different evaluation rules may be selected from different members of the group a.-f. may be selected. Step b) may include generating the set of evaluation rules, which may include the following sub-steps:

b1): providing a learning set of learning measurement curves, acquired by using a learning set of learning body fluids and by monitoring detection reactions of a test substance and the test body fluids. The test body fluids and the detection reactions may be chosen such that the learning measurement curves are acquired with deferring sets of state variables;

b2). identifying a set of candidate evaluation rules and deriving a set of candidate characteristic values 138 from the learning set of learning measurement curves;

b3): determining a correlation between the candidate characteristic values 138 for each candidate evaluation rule and the state variables; and b4) selecting the set of evaluation rules from the set of candidate evaluation rules by accounting for the correlations determined in sub-step b3).

Sub-step b3) may include determining at least one correlation parameter for each candidate evaluation rule for each state variable, especially the Pearson correlation coefficient.

At least one of the two different evaluation rules for determining and/or choosing optimal input parameters (e.g., optimal characteristic values 138, characteristic points) may be used. The characteristic points may include the mentioned end value and/or a minima and/or a maxima of the optical measurement curve, especially of the kinetic curve. Additionally or alternatively, at least one inflection point and/or at least one zero of a function and/or at least one third deviation may be used. In particular, not only the value of the function of the optical measurement curve, especially of the kinetic curve, at the time of such a zero of the function and/or of a derivative may be used but also values of the respective derivatives may be used. For example, the value of the first derivative (e.g., the slope) at a zero of the second derivative (e.g., the inflection point) may be an advantageous input parameter, especially a characteristic value 138. Additionally or alternatively, the points in time 136 of the characteristic points and/or of distinctive positions of the kinetic curve of the optical measurement curve, may be advantageous as input parameter, especially as characteristic value 138.

In each time interval i, at least one correlation parameter, such as a correlation, for at least one of the characteristic values 138 (e.g., an averaged numerical value, especially an input parameter $X_i$) of the optical measurement curve of a function curve, as well as of the first derivative and/or the second derivative and/or the third derivative of the measurement curve and/or the optical measurement curve with the glucose concentration and/or with different other parameters, especially with different state variables (e.g., with the hematocrit value of the used blood) may be determined.

The Pearson correlation coefficient may have arbitrary values between one, over 0, to −1. 1 may indicate a strong correlation, 0 may indicate no correlation, and −1 may indicate a strong anti-correlation.

Figure 2A:
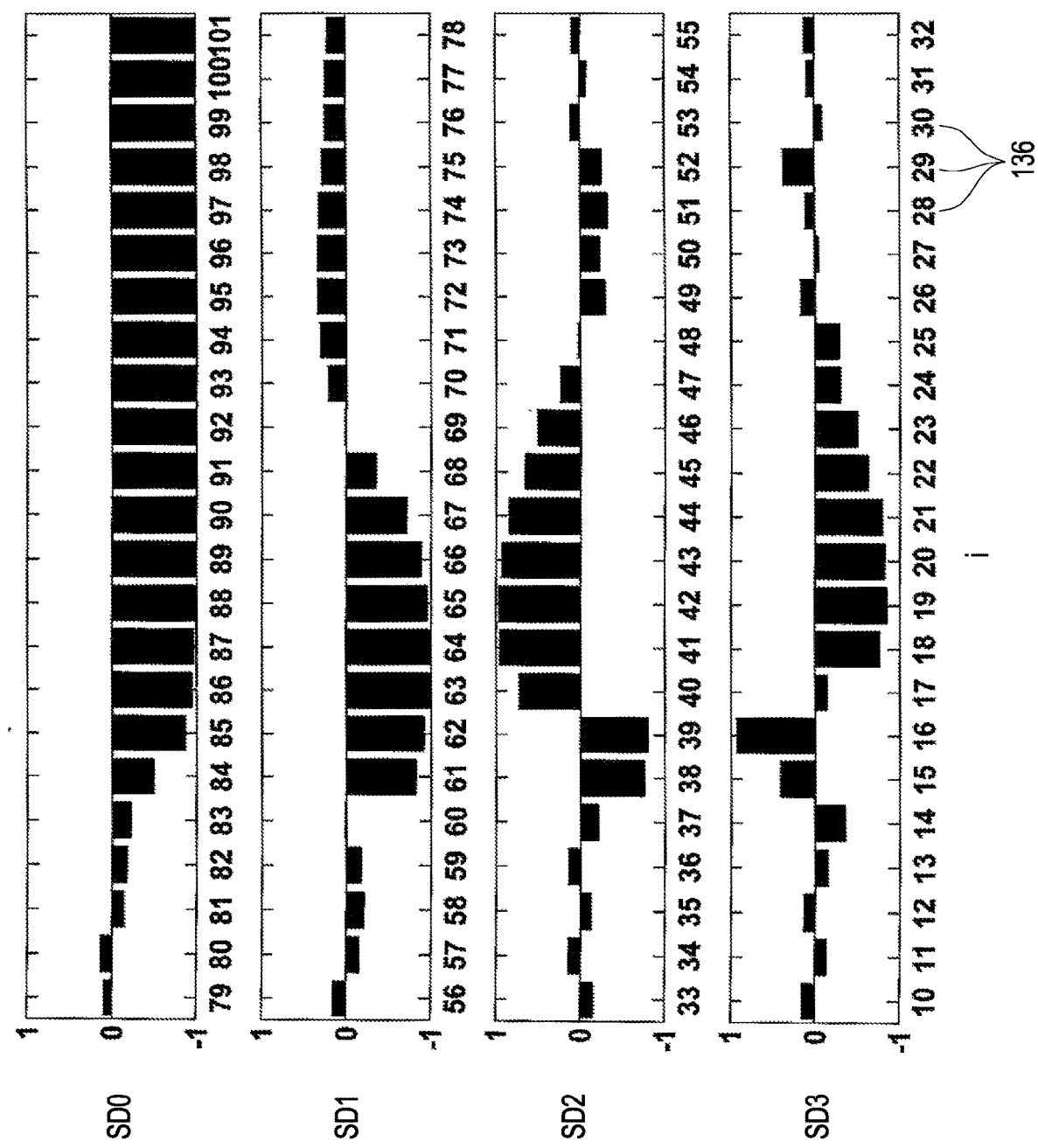
FIGS. 2A-2D show diagrams of an exemplary method of detecting an analyte in a body fluid sample.

FIG. 2A shows correlation coefficients of an optical measurement curve of a test element 118, especially of a test strip to be used with the Accu-Chek® Active system, with the glucose concentration for each input parameter $X_i$. FIG. 2A shows a correlation between the optical measurement curve SD0 (e.g., an original curve), and the glucose concentration in the upper diagram. Below, the correlation of the first derivative SD1, the correlation of the second derivative SD2, and the correlation of the third derivative SD3 with the glucose concentration are shown. The x-axis may correspond to different time intervals i, and the y-axis may correspond to the Pearson correlation coefficient. The data was taken using a test element for an Accu-Chek® Active system as test element 118.

In FIG. 2A, one may identify clearly a strong anti-correlation of the input parameters $X_{85}$-$X_{101}$ of the optical measurement curve, especially of the original curve SD0. Furthermore, one may recognize an anti-correlation in the first derivative SD1 for the input parameters $X_{62}$-$X_{66}$ or a correlation in the second derivative SD12 for the input parameters $X_{41}$-$X_{43}$. The correlation in the original curve, in the zero derivative SD0, with the glucose concentration for high times may not be surprising as this may refer to determining the glucose concentration by using the end value. Furthermore, correlations in time intervals of the first derivative may not be surprising as the gradient of the optical measurement curve for small times may be used for an evaluation. For example, one may use the first derivative instead of the end value for evaluating the optical measurement curves. Interferences, caused by state variables, may influence the first derivative signal too much, thus, a prediction of the glucose concentration may be too inexact.

In sub-step b4), a Merit value may be calculated for each correlation. The selecting of the set of evaluation rules from the set of candidate evaluation rules may be performed by accounting for the Merit values. In sub-step b4), a candidate evaluation rule may be determined to be an evaluation rule if the corresponding correlation determined in sub-step b3) may fulfill at least one predetermined condition. A method for use in a multivariate data analysis may be the so-called "partial least squares regression" (PLS).

As shown in FIG. 2A, the end value may be combined with at least one gradient value (e.g., a first derivative). For understanding, which parameters (e.g., which characteristic values 138) may be suiting best for a multivariate analysis, a correlation analysis may be useful. Within generating the set of evaluation rules, input parameters and/or characteristic values 138 may be chosen, which may correlate maximally with the analyte concentration and probably not with other state variables, respectively.

Figure 2B:
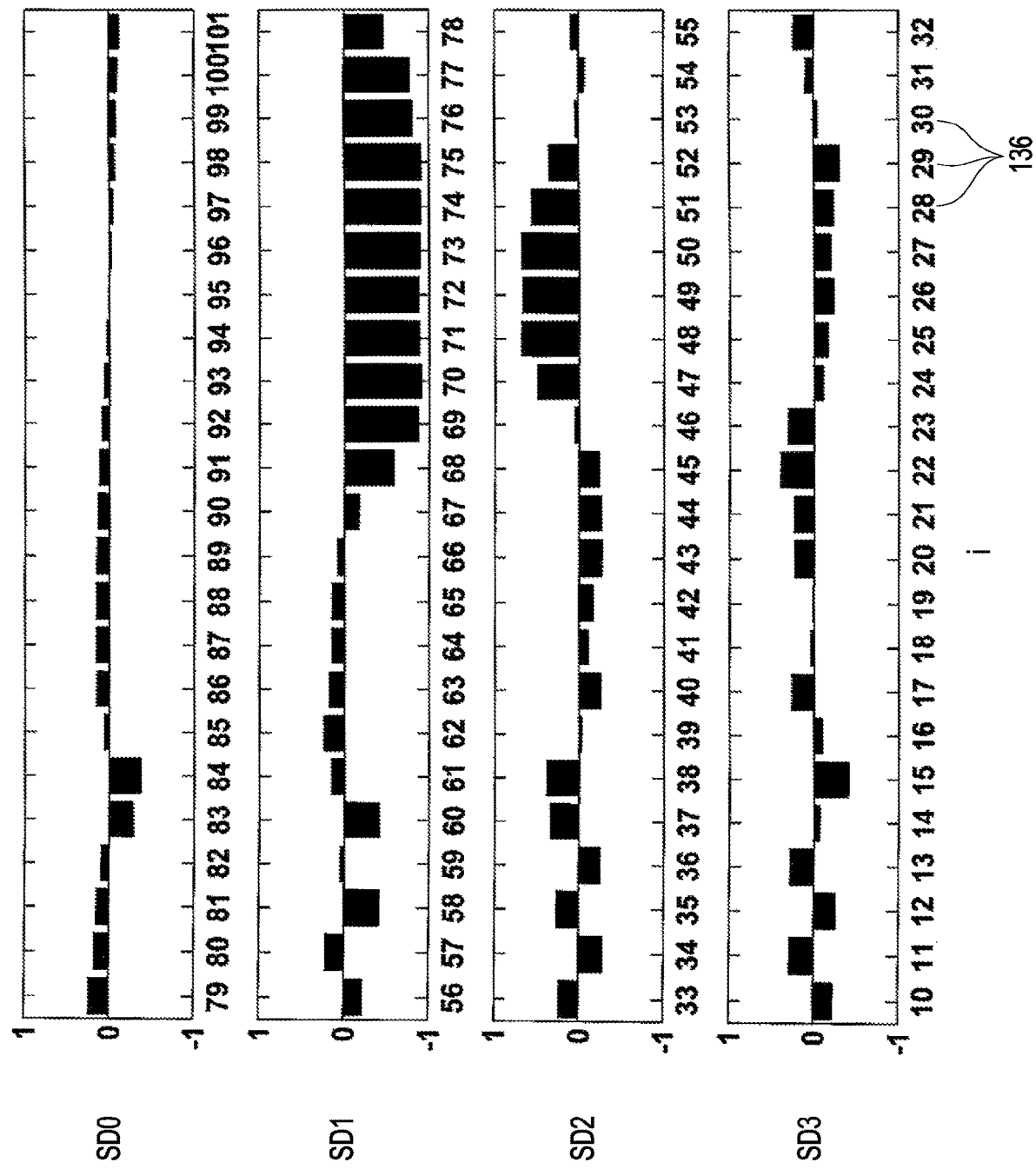
Figure 2:
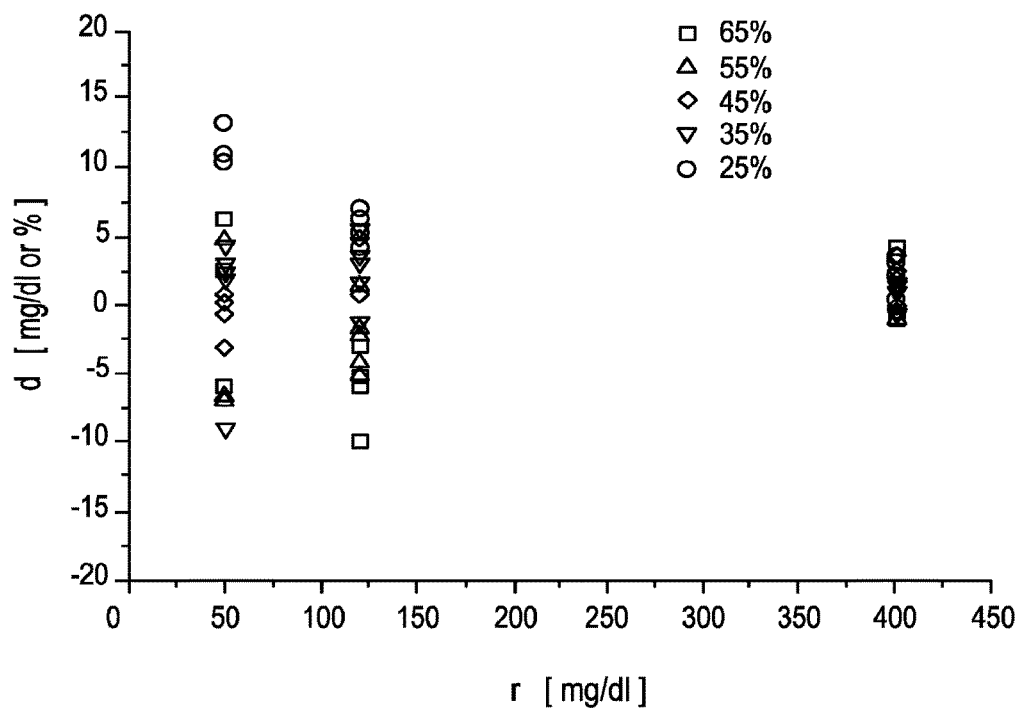
Figure 2:
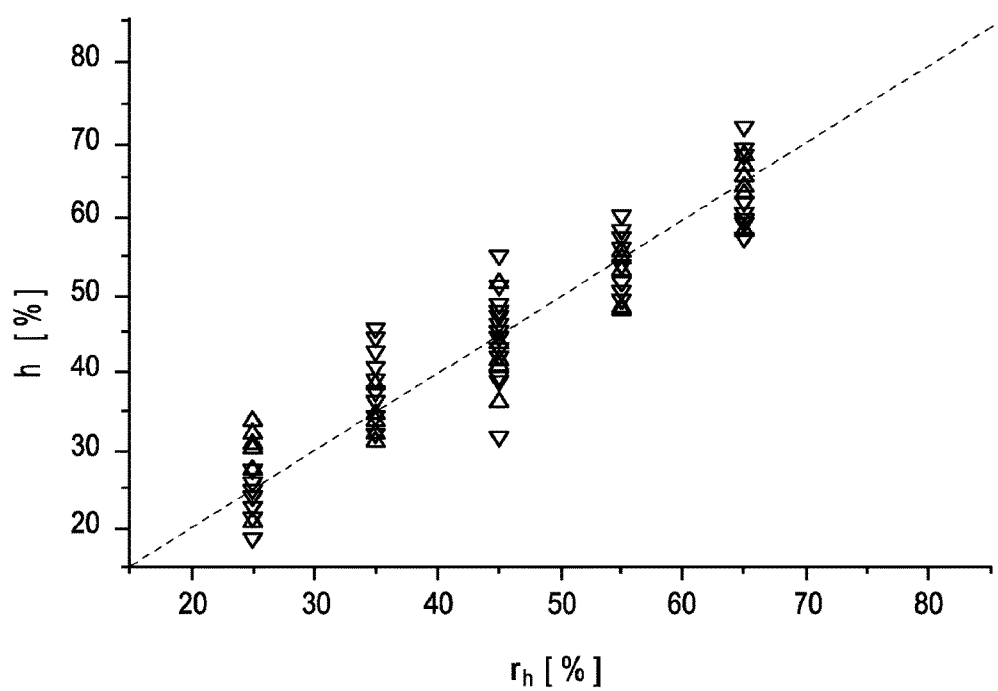

FIG. 2B shows for the identical optical measurement curve for the identical data set, as for FIG. 2A not the correlation with the glucose concentration, but the correlation coefficient referring to the hematocrit concentration (e.g., to a hematocrit value). FIG. 2B particularly shows that the parameter $X_{69}$, the first derivative of the optical measurement curve for a time interval between 7.2-8.7 seconds, correlates very strong with the hematocrit concentration, but basically not, as shown in FIG. 2A, with the glucose concentration.

For example, by using the parameters $X_{83}$ and $X_{69}$ as characteristic values 138, an influence of hematocrit may be divided from an influence of the glucose concentration by smart analysis, especially by using the multivariate analysis. By using these two parameters together with the end value in a PLS analysis, one may get already a significant improvement of the prediction of the glucose concentration.

FIG. 2B shows, similar to FIG. 2A, correlations between the optical measurement curve SD0, the first derivative SD1, the second derivative SD2, the third derivative SD3, and the hematocrit concentration. The x-axis may correspond to the different time intervals, indicated by i. The y-axis may correspond to the Pearson correlation coefficient. i may be related to at least one index of a parameter matrix. The data shown in FIG. 2B may be related to measurements using test strips for an Accu-Chek® Active system.

FIG. 2C shows the deviation d in mg/dL or % against a reference glucose concentration in mg/dL for different hematocrit values. The different hematocrit values are indicated by differently shaped symbols as described in the legend of FIG. 2C. In particular, FIG. 2C in particular shows the difference between the glucose concentration determined by a method as disclosed herein using the multivariate analysis and a reference concentration, especially a reference glucose concentration, for different hematocrit values. The measurements according to FIG. 2C are carried out by using a sample analysis device 110 as disclosed herein, especially by using an Accu-Chek® Active system. FIG. 2C shows the deviation d of the prediction of the glucose concentration from the reference glucose concentration r as reference value, where the predicted glucose concentrations may be determined by using the PLS analysis based on the end value and the parameter $X_{69}$ and $X_{83}$. By deriving the median of the absolute deviation and/or of the relative deviation one may get as total error a value of 3.5, compared to a value of 6.3 by using an end value criterion known from prior art.

By using methods as disclosed herein, especially by using the multivariate evaluation algorithm, one may be able to distinguish between changes of the optical measurement curve (e.g., of the kinetic curve, such as changes of the signal) induced by the glucose concentration and induced by the hematocrit concentration.

The methods herein may provide the possibility for a prediction, especially at least a rough prediction, of determining the hematocrit concentration out of the optical measurement curve (e.g., out of the kinetic curve). This is shown in FIG. 2D. In particular, FIG. 2D shows a predicted hematocrit h in % against a reference hematocrit rh in %. The different symbols may reflect different glucose concentrations.

FIG. 2D specifically shows the predicted hematocrit determined out of the parameters (e.g., input parameters) $X_{69}$ and $X_{85}$, and the end value compared to an actual hematocrit value, especially the reference hematocrit rh exemplary for a test strip 120 to be used with the Accu-Chek® Active system for glucose, a test element 118 specified for analyzing glucose.

Other methods herein can be used for characterizing a body fluid sample, where such methods include the following steps:

A): bringing the body fluid sample into contact with at least one test substance, thereby initiating a detection reaction of the test substance and the body fluid sample. The detection reaction is known to be influenced by a set of state variables, where each state variable characterizes at least one of a state of the body fluid sample and the condition of the detection reaction;

B): monitoring a time development of at least one measurement value indicating a progress of the detection reaction, thereby recording an optical measurement curve containing a plurality of the measurement values acquired at different points in time 136; and C): evaluating the optical measurement curve by using a method of detecting an analyte in the body fluid sample by the methods disclosed above.

In the methods of detecting an analyte in the body fluid sample, evaluation rules may be used as disclosed herein. The best parameters X, may be searched for the multivariate data analysis. Accordingly, the respective numeric coefficient $a_i$ of a multivariate analysis for a code curve may be found as numeric values of the coefficients.

Figure 3:
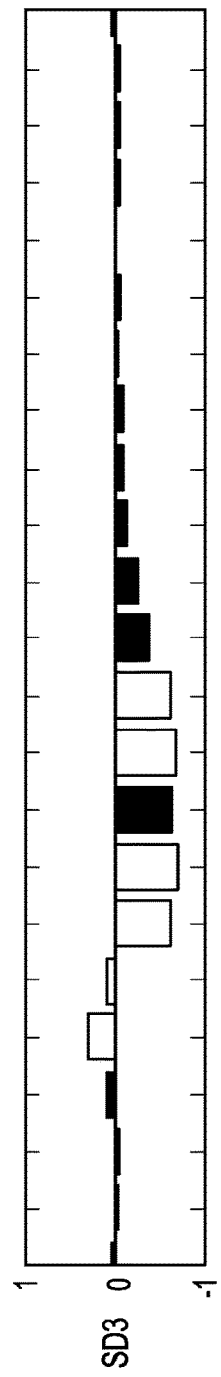
FIG. 3 shows correlations between a remission and a glucose concentration and correlations between derivatives of the remission and the glucose concentration of another exemplary method.
Figure 3:
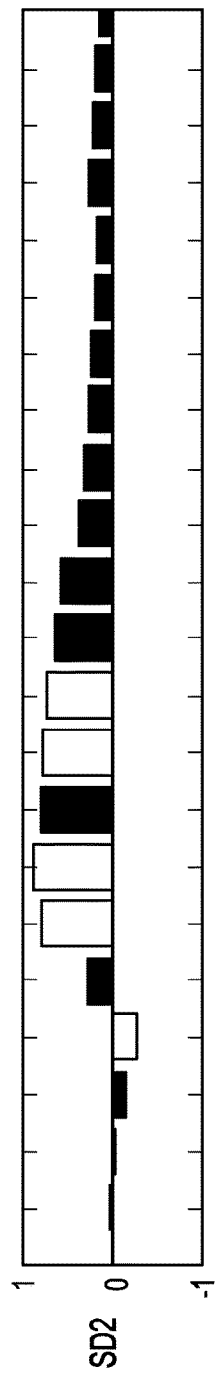
Figure 3:
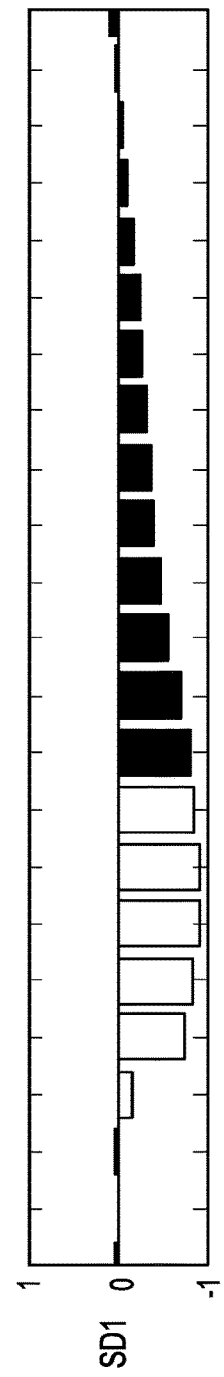
Figure 3:
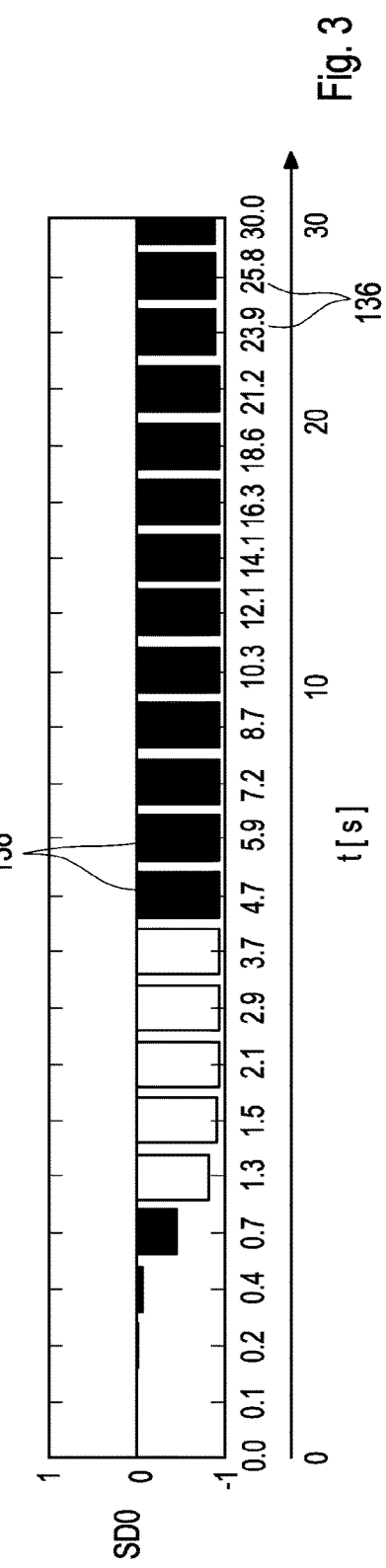

FIG. 3 shows correlations for another exemplary method. In particular, FIG. 3 shows correlations between an optical measurement curve (e.g., an original remission kinetic curve SD0, especially original data), the first derivative (e.g., the slope SD1), the second derivative (e.g., the curvature SD2), the third derivative SD3, and the glucose concentration, especially for test strips 120. The y-axis relates to the Pearson correlation coefficient, and the x-axis relates to the time t in seconds. The white marked intervals i may indicate the time intervals chosen for the characteristic values 138. FIG. 3 shows 22 white marked intervals, thus 22 characteristic values 138 may be used in the further analysis such as a multivariate analysis. Here, a suppression of an influence of the temperature on the optical measurement curve (e.g., on the kinetic curve) may be compensated. At least one, especially several, features described above may be used. For example, the methods of determining and/or identification of the input parameters and/or of the characteristic values 138 may be used. As a result, the white marked time intervals may be advantageous due to using the methods herein for selecting the evaluation rules and/or of characteristic values 138.

In the methods, carbanicotinamide adenine nucleotide (cNAD) may serve as co-factor for an enzyme-based detection, as described in von Ketteler et al. (2012) supra. By using a cNAD test substance, cNADH may be generated proportional to the glucose concentration. cNADH may not only absorb ultraviolet (UV) light with a wavelength of 360 nm during excitation with light but also may emit fluorescence light, especially fluorescence light with an emission maximum at 460 nm. The fluorescence light may be detected by using an optical filter, such as a simple optical filter, in front of a photodiode as detector 130. Alternatively or additionally, the detecting of the remission and/or the detection of the fluorescence light may be advantageous for use in analyzing the sample, in particular in the multivariate analysis.

Figure 4:
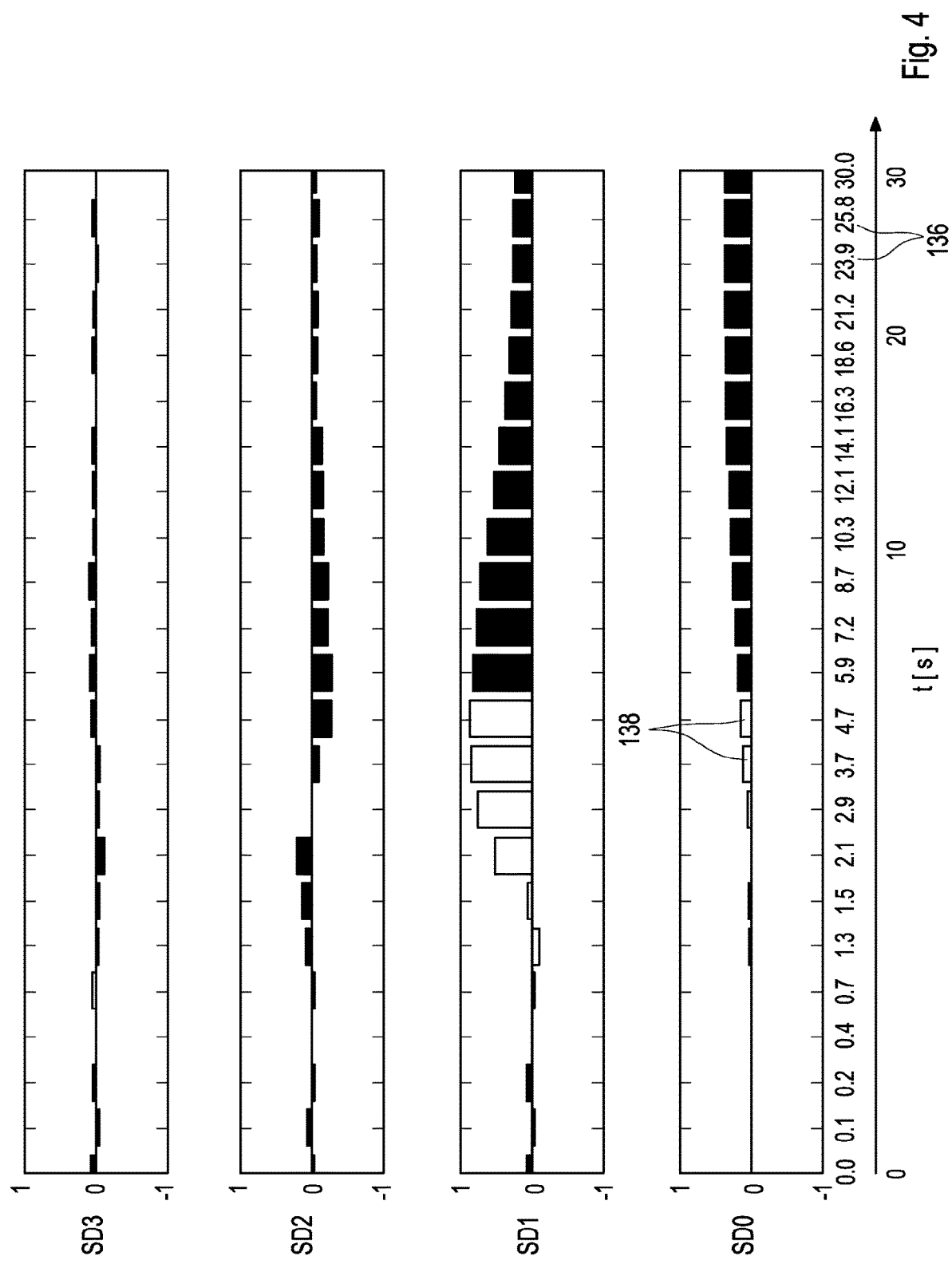
FIG. 4 shows correlations between a fluorescence and a glucose concentration, as well as shows correlations between derivatives of the fluorescence and the glucose concentration of another exemplary method.

FIG. 4 shows correlations between the optical measurement curve (e.g., an original fluorescence kinetic curve SD0), the first derivative SD1 (e.g., the slope), the second derivative SD2 (e.g., the curvature), the third derivative SD3, and the glucose concentration for a cNAD strip. The white marked time intervals were chosen for a further analysis such as for a multivariate analysis. FIG. 4 also shows correlation coefficients against a time tin s. Input parameters (e.g., characteristic values 138) may be deduced from a correlation analysis. The correlation analysis is shown in FIG. 4. These input parameters may alternatively or additionally be used in a mixture with remission data, as shown in FIG. 3.

Using the multivariate data analysis as disclosed herein for predicting a glucose concentration may reduce a dependency, even a strong dependency, of a prediction of a glucose concentration on a temperature. The strong dependency of the prediction of the glucose concentration on the temperature for a method using only the end value, (e.g., as known from prior art) may be in average 1.76%/K. The dependency by using the methods herein (e.g., by using a PLS analysis on basis of the optical measurement curve, such as the kinetic curve, of the remission) may be 0.47%/K. The dependency when using the methods herein (e.g., when using the PLS analysis of the optical measurement curve, such as the kinetic curve, generated by photometry and fluorescence) may be 0.02%/K. This reduction of the dependency is shown in FIG. 5.

Figure 5:
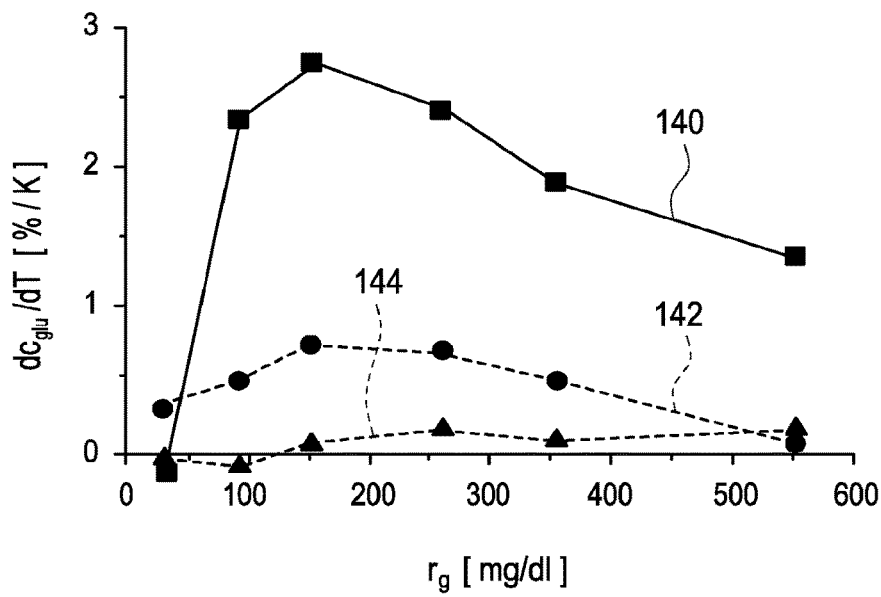
FIG. 5 shows a diagram presenting advantages of the exemplary methods.
Figure 6:
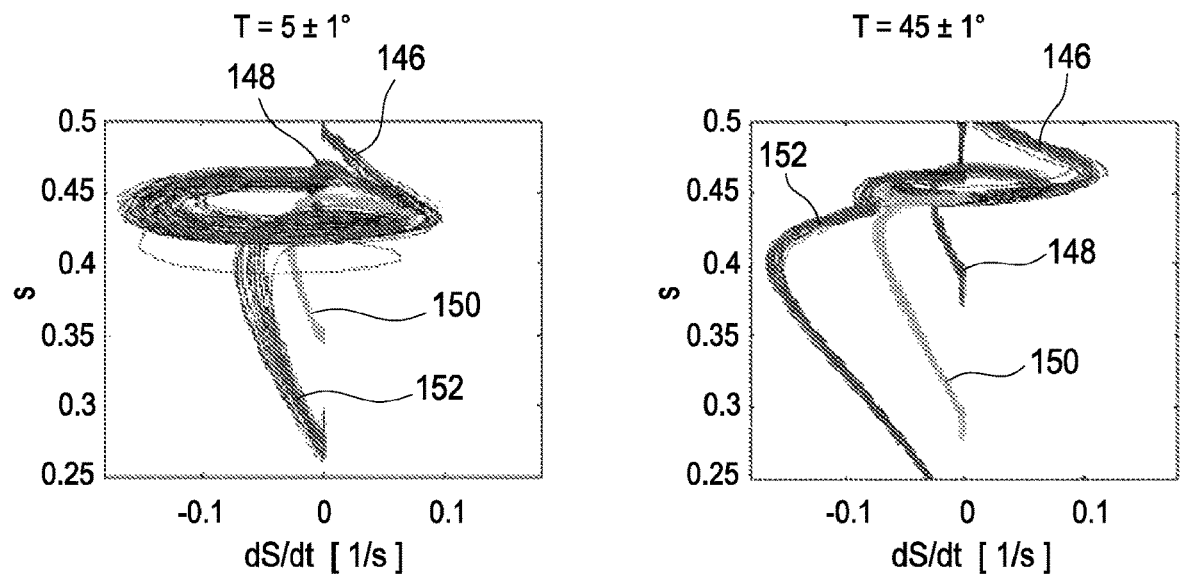
FIGS. 6A-6B show phase plots of a first order derivative of a remission with respect to a time over a remission for another exemplary method for two different temperatures.

FIG. 5 shows the dependency of the deviation between a prediction of the glucose concentration and a real concentration of glucose on the influence of strong temperature changes $dc_{glu}/dT$ in %/K against the real glucose concentration $r_g$ in mg/dl. Curve 140 refers to a measurement using an end point detection (e.g., the end value criterion, known from prior art), where the dependency on a temperature may be about 1.76%/K. Curve 142 shows a measurement using the methods herein, especially using the multivariate analysis, by using the remission, particularly showing a dependency on a temperature of 0.47%/K. Curve 144 refers to a measurement using methods herein and using the remission and the fluorescence, wherein the dependency from a temperature may be 0.02%/K. The deviations may achieve significantly more than 2%/K for using a method known from prior art with end point value detection. The deviation may be reduced by using the multivariate analysis, in average less than about 1%/K, especially by using the remission, and less than about 0.2%/K, by using the remission and the fluorescence. Thus, by using the methods herein, compensation of deviations due to temperature may be possible without using a temperature sensor, such as only by using the optical measurement curve (e.g., the kinetic curve). In the methods herein, no temperature sensor may be used for detecting the analyte in the body fluid sample.

FIGS. 3 and 4 show methods for selection of at least one of the evaluation rules. FIGS. 6A and 6B show an advantageous method of determining characteristic values 138 (e.g., of the parameters), which may be called the phase space method. The phase space method may include generating a phase plot, especially at least one phase space curve, of at least two derivatives of different order of the optical measurement curve. Auxiliary quantities may be derived from the phase plot. In some instances, the auxiliary quantities may include at least one input parameter, especially at least one characteristic value 138. At every point in time, especially of the optical measurement curve, a pair of data including at least one point out of the optical measurement curve and/or at least one point of at least one derivative of the optical measurement curve may be plotted.

FIGS. 6A and 6B show examples of phase plots. The phase plot may also be called phase space diagram. The phase plot may include pairs of points. One data point may relate to one point in time in the optical measurement curve (e.g., in the kinetic curve). The pair of points may include a remission and the first derivative of the remission with respect to time. FIGS. 6A and 6B show phase plots, where remission values S are plotted over the first derivative of the remission with respect to time dS/dt in 1/s, thus, over the slope of the optical measurement curve (e.g., over the slope of the kinetic curve). FIG. 6A shows a phase plot for a temperature of 5±1° C. for different glucose concentrations, and FIG. 6B shows a phase plot for a temperature of 45±1° C. for different glucose concentrations. The curves 146 belong to a glucose concentration of 0±5 mg/dl, the curves 148 belong to a glucose concentration of 89±5 mg/dl, the curves 150 belong to a glucose concentration of 258±5 mg/dl, and the curves 152 belong to a glucose concentration of 554±5 mg/dl. Curve 146, curve 148, curve 150 and curve 152 may be phase space curves. FIGS. 6A and 6B show phase plots including phase space curves. The curve may start at a point (0-0) and may propagate on loops to a value near the value of dS/dt≈0. dS/dt≈0 may be the basis for an evaluation using a remission value by using a stop criterion. The loops before reaching the end point in a phase plot may include information about at least one state variable, especially about the temperature, which may be used for a compensation by the multivariate analysis (e.g., by a multivariate evaluation). For example, one may ask at which remission value the slope may have its minimum (e.g., at S=0.44 or at S=0.40). S=0.44 may indicate a low temperature, especially almost independent on a concentration (e.g., on a glucose concentration). S=0.40 may indicate a high concentration (e.g., a high glucose concentration) and a high temperature. The point with the smallest, especially negative, slope, the furthest left point of the phase plot, may be helpful in all its information with respect to its remission value and/or its first and/or second and/or third derivative and/or its point in time at which this point may be reached.

Additionally or alternatively, values directly generated by using the phase plot may be used (e.g., a position of a center of the phase space curve, especially coordinates of a center of the phase space curve, of the phase plot, a length of the phase space curve, and/or a length of the phase space curve, and/or a phase space volume and/or a phase space area and/or points with a maximal distance to the center of the phase space curve and/or a mean squared distance from the origin of the phase space, indicating dS/dt=0 and/or other properties of the phase space plot). FIGS. 6A and 6B show that a slope and/or an end value in phase space (e.g., in a phase space curve and/or in a phase space plot) may depend on the glucose concentration. In particular, FIGS. 6A and 6B show that phase plots and/or phase space curves may look different for different temperatures. Differences of phase plots for different temperatures may be analyzed by using mathematical methods. For example, mathematical methods may be used for distinguishing phase plots and/or phase space curves in terms of at least one state variable, especially in terms of the temperature, by calculating the value derived from the phase plot as described above.

An advantage of the multivariate analysis may be a simultaneous determination of calibration data and/or of at least one target value and/or of at least one state value. The multivariate analysis may alternatively or additionally include a consecutive procedure. A consecutive procedure may be used in a method using a phase plot (e.g., in the phase space analysis as described above). For example, an end value may be determined out of the optical measurement curve (e.g., out of the kinetic curve), where the end value may lead to a prediction of the glucose concentration. A value of a prediction of the glucose concentration may be corrected depending on a presence of other criteria of the optical measurement curve (e.g., of the kinetic curve). The method of correcting the predicted glucose concentration may include at least one weighting. For example, the weighting may be done in respect to a temperature and/or a hematocrit value and/or a humidity and/or an enzyme activity and/or a date of expiry and/or a marker of an endurance, where at least one of these properties may be determined out of the optical measurement curve (e.g., out of the kinetic curve). Alternatively, the weighting may include at least one other property of the method and/or of the device and/or of the optical measurement curve.

The methods herein may include a determination of parts of the optical measurement curve that may be used for calculating different parameters of the characteristic values 138. The calculation may include at least one weighting. The weighting may be used for stronger weighting of selected parameters of selected characteristic values 138. For example, a parameter, especially a characteristic value 138, related to hematocrit may be determined by using a first part of the optical measurement curve. A parameter, especially a characteristic value 138, being related to a dependency on a temperature and/or on another state variable may be determined by using at least one part of the optical measurement curve being different from the first part of the optical measurement curve. The methods herein may include determining parts of the optical measurement curve (e.g., a time interval) and a correlation of the parts of the optical measurement curve with at least one parameter, especially a correlation of the part of the optical measurement curve with at least one state variable.

The PLS analysis described above may be a linear multivariate method. The relation between the glucose concentration and the remission and/or the fluorescence may not be linear, as may be seen on calibration curves based on the end value criterion. But using the PLS analysis may lead to an improvement. The improvement may be caused by the quadratic term in the multivariate analysis (e.g., in the algorithm). Additionally or alternatively, the optical measurement curve (e.g., the original kinetic curve) may be transformed by a term being not proportional to the remission, but by a term being proportional to $1/R$ and/or $1/R^2$ and/or log(R) and/or $R^{1/2}$ and/or $R^{3/2}$ and/or a similar term, where R may be the remission.

Additionally or alternatively, inherent non-linear multivariate methods may be used. Inherent non-linear multivariate methods may include a neural network with sigmoid neurons and/or support-vector machines. Thus, the methods may include at least one neural network and/or at least one support-vector machine. Alternatively or additionally, genetic algorithms may be used in the methods herein.

The methods herein may include at least one correlation analysis and/or at least one determination of characteristic values 138 and/or a search in the phase space and/or a renormalization by non-linear functions and/or the use of PLS algorithms and/or the use of non-linear classification methods and/or regression methods as ANNs and/or SVMs.

The characteristic values 138 may be independent. The correlation analysis and/or the calculation of the merit function may be used for avoiding dependencies of the characteristic values 138.

The optical measurement curve (e.g., at least one kinetic curve) may be linearized. For linearization, a model for a prediction of the glucose concentration out of the remission value may be derived by using an end value evaluation (e.g., based on a –2% end value) out of the optical measurement curve (e.g., out of a precision set of data). This model may be applied to the whole optical measurement curve (e.g., to the whole kinetic curve) afterwards. Furthermore, the methods may include an averaging of at least a part of the optical measurement curve (e.g., of the kinetic curve). Furthermore, at least one merit-function, especially for the linearized optical measurement curve (e.g., for the linearized set of data) may be used. For example, in the linearized optical measurement curve, especially in the linearized set of data, a correlation analysis may be executed for each temperature for the characteristic values 138 (e.g., for characteristic curve parameters). The correlation analysis may include a calculation of correlations with a glucose concentration and/or a hematocrit concentration and/or a humidity. Merit-functions may be derived out of the correlations (e.g., out of correlation values), especially out of the Pearson correlation coefficients by using the following formula:

$$\text{Merit value} = \frac{\text{correlation}^2}{(|\text{correlation}_{glucose}| + |\text{correlation}_{hematocrit}| + |\text{correlation}_{humidity}|)}.$$

The correlation may be the correlation coefficient for the concentration of glucose correlation$_{glucose}$ or the correlation coefficient for the hematocrit concentration correlation$_{hematocrit}$ or the correlation coefficient for the humidity concentration correlation$_{humidity}$. The Merit value may be used for extracting the characteristic values 138.

The methods herein thus include a multivariate analysis for evaluating an optical measurement curve, especially a kinetic curve such as a kinetic curve for determining a glucose value/concentration generated by an optical measurement, but also by other types of measurements. The first characteristic value or the second characteristic value may not be the dry empty value of the measurement (i.e., may be different from a dry empty value).

For a successful use of the multivariate analysis, a correlation being as significant as possible between the target values and/or the state variables, especially a glucose concentration, and different state variables and/or disturbing factors may be useful. The characteristic values 138 generated thereby may be used together with, for example, statistically generated, concrete number values for coefficients (e.g., the Pearson correlation coefficient) for implementing in a simple algorithm in the devices herein. The precision may be increased by taking into account cross-terms and/or terms of higher order.

In the methods herein, the characteristic values 138 may be different parameters. The different parameters may be weighted with different weights per parameter. The characteristic values 138 may be extracted from defined parts of the optical measurement curve and/or may be single characteristic points of the optical measurement curves (e.g., of the kinetic curve). The methods herein may include determining the parts of the optical measurement curve and their assignment for getting the parameters, especially for getting the characteristic values 138.

The optical measurement curve (e.g., the kinetic curve) may be divided in parts of the optical measurement curve, where this may enable applying individual algorithms on the parts of the optical measurement curve. For example, defined time intervals (e.g., time windows) in the optical measurement curve may be attached to an influence of concrete state variables (e.g., concrete disturbance values). The methods herein may include a combination of determined parameters (e.g., a combination of the characteristic values 138).

A selection of the parts of the optical measurement curve (e.g., of the time intervals) may be made by calculating the merit function as part of the correlation analysis. The methods herein also may include the end value criterion. The characteristic values 138 may be independent from each other. The target variable Y may be the analyte concentration, which may be determined. The characteristic values 138 may be determined by using the evaluation rules. The characteristic value 138 may be characteristic for at least one variable (e.g., for at least one state variable, especially for at least one target variable, and even for the analyte concentration). The characteristic value 138 may be different from the analyte concentration, especially different from the glucose concentration. The multivariate analysis may be done with at least two different characteristic values 138 and/or with at least two different variables. At least one variable (e.g., at least one characteristic value 138) may be different from the analyte concentration. The variable may be determined out of the characteristic value 138 by using at least one evaluation rule. The characteristic value 138 being different from the analyte concentration may be determined by using the evaluation rule. The multivariate analysis may use at least one variable being different from the analyte concentration. The variable being different from the analyte concentration may be determined by using the evaluation rule.

Figure 7:
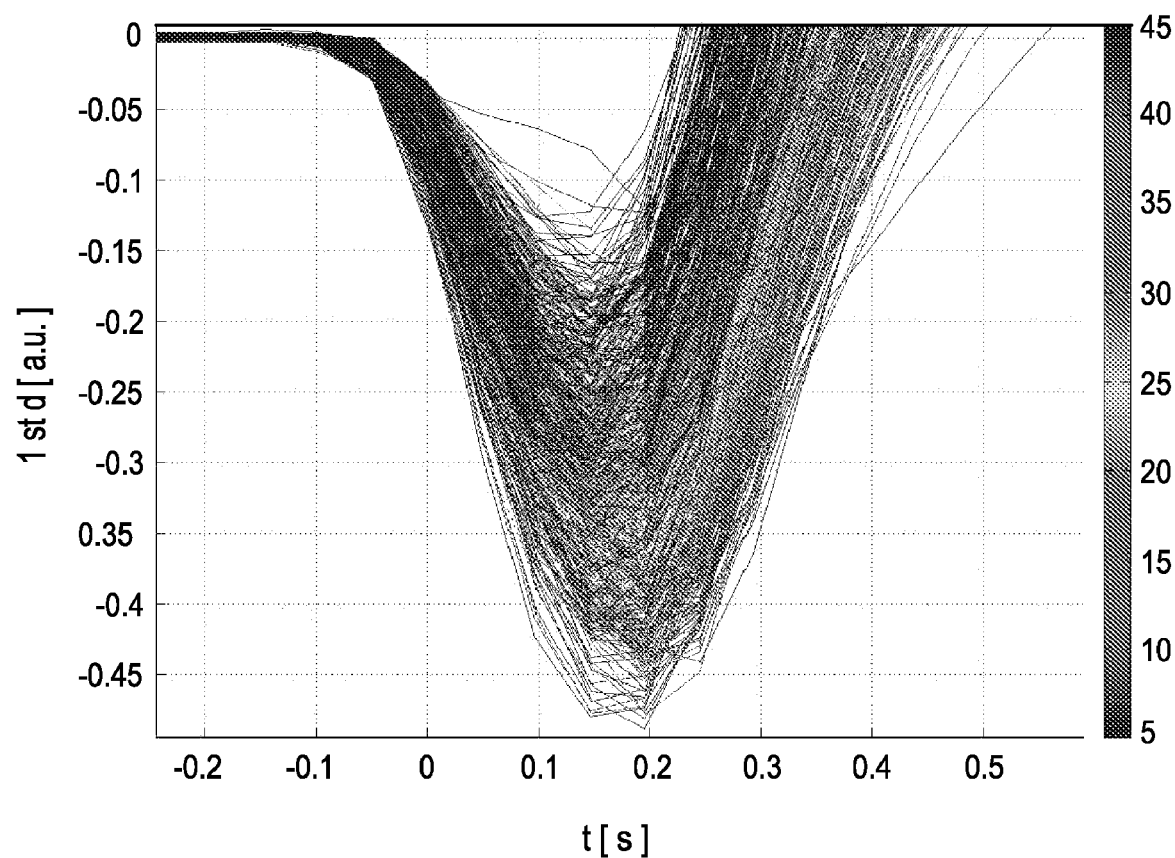
FIG. 7 shows a diagram of a further exemplary method of detecting an analyte in a body fluid sample.

FIG. 7 shows another aspect of the methods herein. The state variables may include at least one disturbance value. Influences of disturbance values on the measurement values, especially on values for the glucose concentration, may be compensated by an analysis of at least one derivative (e.g., of more than two derivatives) of the optical measurement curve and/or of the measurement curve.

An analysis of derivatives of the measurement curve, especially of the optical measurement curve such as a kinetic curve, may show correlations with the glucose concentration as well as correlations with disturbance values (e.g., state variables) as the temperature and/or the humidity, especially an air humidity, and/or the hematocrit concentration. In particular, at very early times of the kinetic curve (e.g., directly after combining the test substance and the body fluid sample), it may be probable that there may be no correlation with the glucose concentration. But directly starting diffusion processes and/or dissolution processes usually may cause a dependency on the disturbance values. These dependencies on the disturbance values may be visible, analogous to an evaluation of the glucose concentration, by a structure of the derivatives of the measurement curve, especially of the optical measurement curve (e.g., in a maxima or a minimum). This correlation with at least one disturbance value may be used for a compensation from the disturbance value and/or from the disturbance effect, especially for calculating a compensation. For example, a first minimum of the first derivate may depend on a temperature and/or on the hematocrit concentration, but may be independent on the glucose concentration. This phenomena may be referred to as the wetting dip or wetting step in the measurement curve and/or in a first order or higher order derivative of the measurement curve. A combination of this phenomenon, especially of the compensation, with the end value criterion discussed above may lead to a value for the glucose concentration that may be corrected from influences caused by the hematocrit concentration.

The methods may include a multivariate analysis, especially a bivariate analysis. A formula for deriving the glucose concentration may be searched "manually" by comparing measurement curves and/or derivatives of measurement curves and/or influences of disturbance values and/or state variables by a skilled person. In particular, FIG. 7 in particular shows the first derivative 1st d of a measurement curve, especially of an optical measurement curve, in arbitrary units, against the time t, especially against the measurement time t, in seconds. FIG. 7 further shows an example of measurement values depending on the temperature and on the glucose concentration, which may at early times only depend on the temperature. Similar effects may be present also for other disturbance values (e.g., for the hematocrit concentration). FIG. 7 also shows the dip, particularly the wetting dip, visible in the first derivative 1st d. The temperatures may vary between about 5° C. and about 45° C. The data includes different glucose concentrations, where they may not be distinguishable at these times, especially at these times of the kinetic curve. Only a dependency on the temperature is clearly visible. By using the depth of the dip a, at least partial, compensation for the temperature dependency may be possible.

Additionally or alternatively, the predetermined multivariate evaluation algorithm may include a procedure that may involve a first-order, a second-order, and/or a higher-order decision tree 154, 164, which may include at least one decision branch that may allow selecting one out of at least two, especially two, alternative procedures based on an assessment whether a predetermined condition may be fulfilled or not. Hereby, the predetermined condition may assess whether a definite value falls within a predetermined range or not and may, thus, offer a decision between performing or not performing a specific procedure or performing the specific procedure under a specific parameter, with a specific parameter set, or within a specific parameter range, wherein the specific parameter may comprise the first or the second characteristic value 138.

As a non-limiting example, the predetermined multivariate evaluation algorithm may include the following function involving a first-order decision tree $f(X_1, X_2)$, $$Y = f(X_1, X_2) = \{g_1(X_2) \text{ for } \text{cond}(X_1); g_2(X_2) \text{ for NOT cond}(X_1)\}, \quad (7)$$

wherein, depending on the assessment whether the predetermined condition $\text{cond}(X_1)$, which may depend on the first characteristic value $X_1$, may be fulfilled or not, the estimate value for target variable Y may be derived according to Equation (7) by either using a first function $g_1(X_2)$ or an alternative second function $g_2(X2)$, which both may depend on the second characteristic value $X_2$.

Figure 8:
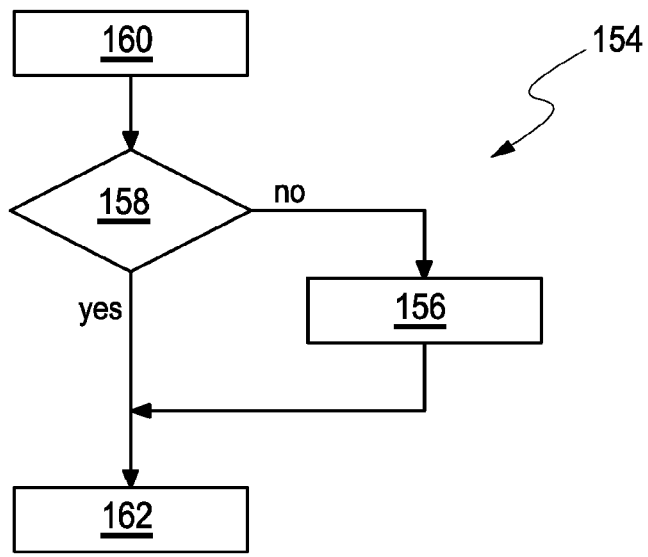
FIG. 8 shows a scheme of a further exemplary method of detecting an analyte in a body fluid sample involving a first decision tree.

As an example related to Equation (7), FIG. 8 shows a first decision tree 154, where a hematocrit correction 156 of the glucose concentration may only be applied outside a predetermined hematocrit range 158 (i.e., only such glucose values may be corrected for which such a correction may be required). In particular, after a determination 160 of the second characteristic value 138 (i.e., the glucose concentration), it may firstly be determined whether the first characteristic value 138 (i.e., the hematocrit) may be inside or outside the predetermined hematocrit range 158, especially covering the range from about 35% to about 50%. However, other values for the predetermined hematocrit range 158 are possible. In this exemplary first decision tree 154, the hematocrit correction 156 of the second characteristic value 138 (i.e., the glucose concentration) may only be applied in case the first characteristic value 138 (i.e. the hematocrit) may be outside the predetermined hematocrit range 158. Thus, a determination 162 of the target value Y involves both the second characteristic value 138 (i.e., the glucose concentration) and the first characteristic value 138 (i.e., the hematocrit).

Consequently, the first decision tree 154 as exemplary depicted in FIG. 8 exhibits the positive effect that only such glucose values are submitted to the hematocrit correction 156 where the hematocrit correction 156 may be required for a further processing of the respective glucose values, in particular for rare cases in which a patient may display a very low or a very high hematocrit. Therefore, this kind of discrimination according to the first decision tree 154 may, thus, help to improve both the speed and the quality of the determination 162 of the target value Y.

Figure 9:
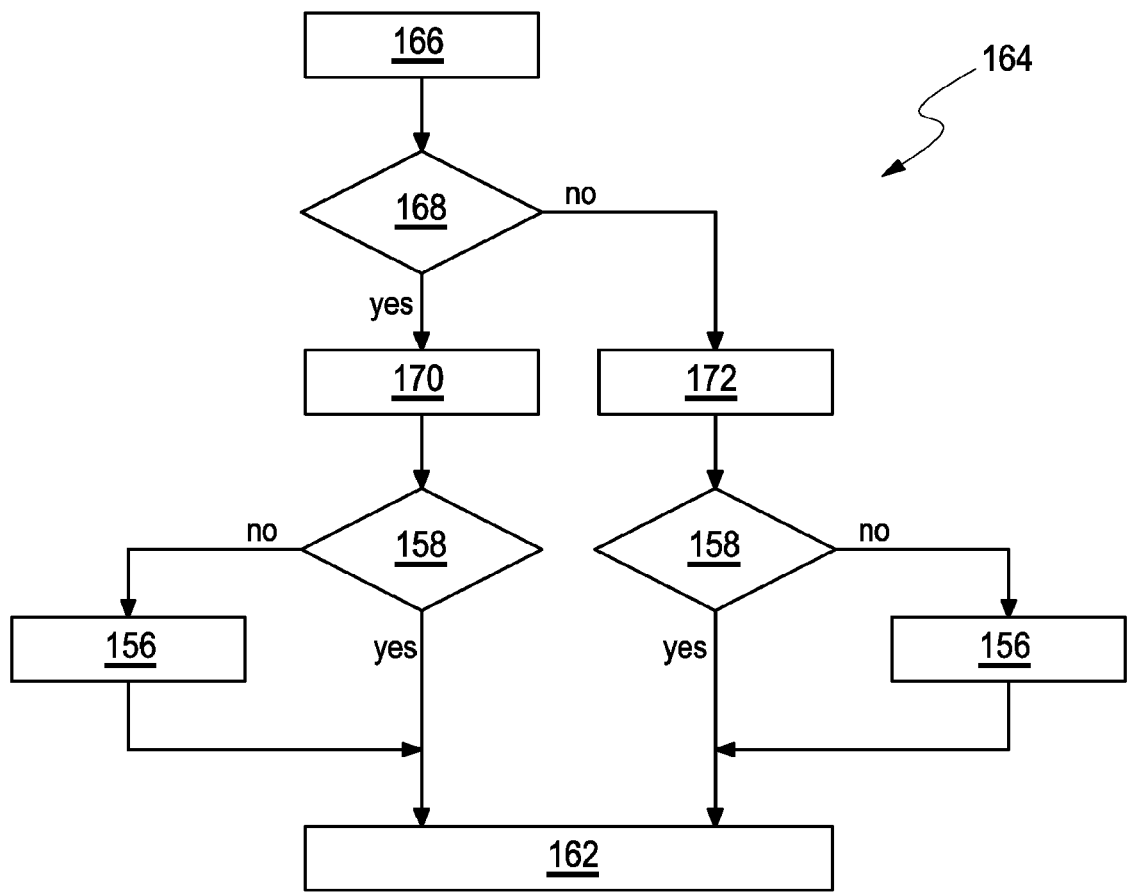
FIG. 9 shows a scheme of a further exemplary method of detecting an analyte in a body fluid sample involving a second decision tree.

As a further example based on Equation (7), the determination 162 of the target value Y may be performed according to a second decision tree 164 as exemplary depicted in FIG. 9. According to the second decision tree 164, the methods may start with a determination 166 of an end value, from which a preliminary value for the second characteristic value 138 (i.e., the glucose concentration) may be derived. According to an assessment whether the preliminary value for the second characteristic value 138 (i.e., the glucose concentration) may fall within a predetermined glucose concentration range 168, firstly, respective first and second threshold values 170, 172 for determining the actual glucose concentration may be selected.

In this example, in case the preliminary value for the glucose concentration may be estimated to be below 100 mg/dl, first and second threshold values 170 of −2%/s for the first threshold and of −0.5%/s for the second threshold may be particularly applied, whereas in case the preliminary value for the glucose concentration may be estimated to be 100 mg/dl or more, the above mentioned values of −5%/s and of −2%/s may be selected as first and second threshold values 172. However, other values the first threshold and for the second threshold may be chosen.

Secondly, in an additional second-order decision branch of the second decision tree 164, a hematocrit correction 156 of the glucose values may only be applied outside the predetermined hematocrit range 158. As already described above in relation to FIG. 8, the hematocrit correction 156 of the glucose concentration may only be performed in case the hematocrit may take a value outside a range of about 35% to about 50%. However, other values are possible.

According to the discrimination as depicted in FIG. 9, the determination 162 of a final value for the glucose concentration may be determined here also with or without hematocrit correction 156 depending on the actual value of the first characteristic value 138 (i.e., the hematocrit). Hereby, the actual values chosen for the hematocrit correction 156 may be independent from the second-order decision branch of the second decision tree 164. Alternatively, for the hematocrit correction 156 actual values may be chosen that might depend on which second-order decision branch of the second decision tree 164 the hematocrit correction 156 may be performed.

Consequently, the second decision tree 164 as exemplary depicted in FIG. 9 may exhibit the positive effects that, firstly, very low glucose values even down to 40 mg/dl or below may be correctly determined, and that, secondly, only such glucose values may be submitted to the hematocrit correction 156, where it may be required in particular for rare cases in which a patient may display a very low or a very high hematocrit. Therefore, this kind of discrimination according to the second decision tree 164 may, thus, help to improve both the speed and the quality of the determination 162 of the final value of the glucose concentration over a much larger range of glucose concentrations than before.

Figure 10:
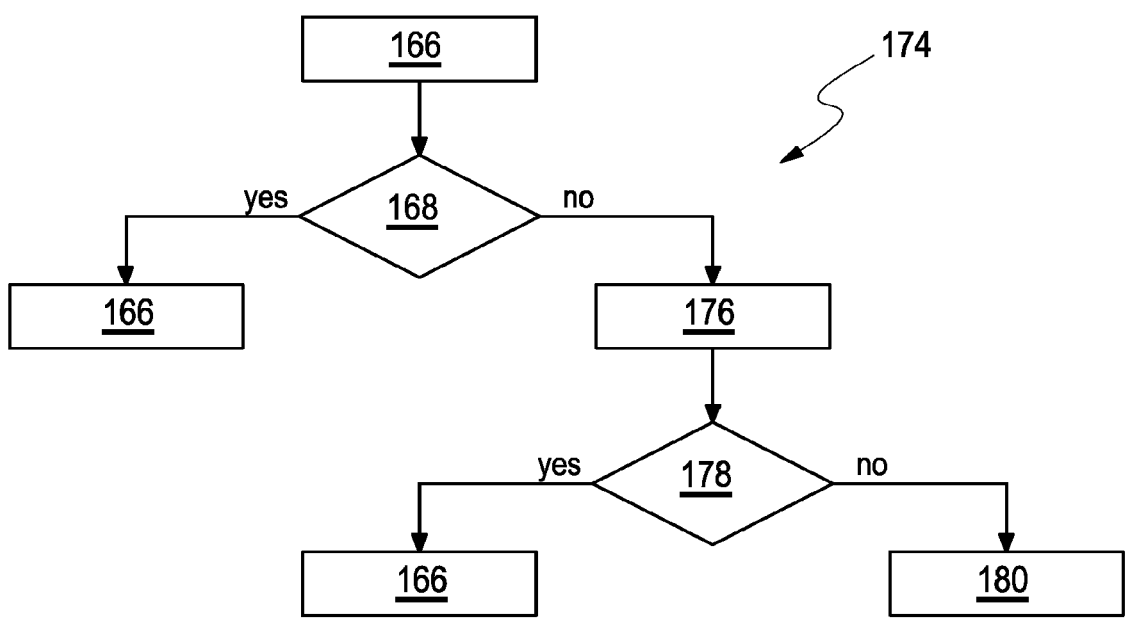
FIG. 10 shows a scheme of a further exemplary method of detecting an analyte in a body fluid sample involving a third decision tree.

As a further example, FIG. 10 shows a third decision tree 174, where from the determination 166 of the end value the preliminary value for the second characteristic value 138 (i.e., the glucose concentration) may be derived. According to an assessment, whether the preliminary value for the glucose concentration may fall within the predetermined glucose concentration range 168, the preliminary value for the glucose concentration as acquired by the determination 166 of the end value may be kept or not. In the latter case, a determination 176 of a decay constant $\Gamma$ or a quantity related to the decay constant $\Gamma$, such as a quantity proportional to the decay constant $\Gamma$ or proportional to the inverse $1/\Gamma$ of the decay constant, may be performed, where the decay constant $\Gamma$ may describe an exponential characteristic within at least an evaluation part of a measurement curve related to the progress of a detection reaction of the glucose concentration. According to a further assessment 178 that might deliver an answer to the question whether the decay constant $\Gamma$ or the quantity related to the decay constant $\Gamma$ may be equal to or exceed a predefined constant $\Gamma 0$, the preliminary value for the glucose concentration as acquired by the determination 166 of the end value may still be kept or not. In the latter case, an additional evaluation procedure 180 for determining the glucose concentration may be performed, where the additional evaluation procedure 180 may take the hematocrit into account. Herein, the additional evaluation procedure 180 may further include another decision branch (not depicted here), which might branch out to different hematocrit evaluation procedures depending on whether the decay constant $\Gamma$ or the quantity related to the decay constant $\Gamma$ may be equal to or exceed a further predefined constant $\Gamma 1$.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

Numbered Embodiments

Embodiment 1

A method for detecting an analyte in a sample of a body fluid, the method comprising the following steps:

providing at least one optical measurement curve, wherein the optical measurement curve contains a plurality of measurement values recorded by monitoring a time development of at least one measurement value indicating a progress of a detection reaction of at least one test substance and the sample of a body fluid, wherein the measurement values contained in the optical measurement curve are acquired at differing points in time, wherein the detection reaction is known to be influenced by a set of state variables, each state variable characterizing at least one of a state of the sample of the body fluid and a condition of the detection reaction;

providing a set of at least two different evaluation rules, each evaluation rule being adapted to derive a characteristic value from the optical measurement curve, thereby deriving a set of characteristic values $X=\{X_i\}_{i=1 \ldots N}$ from the optical measurement curve, the set of characteristic values comprising at least one first characteristic value being derived from the optical measurement curve by using at least one first evaluation rule from the set of evaluation rules and at least one second characteristic value being derived from the optical measurement curve by using at least one second evaluation rule from the set of evaluation rules, the second evaluation rule being different from the first evaluation rule;

performing at least one multivariate analysis of the at least one first characteristic value and the at least one second characteristic value by using at least one predetermined multivariate evaluation algorithm, the multivariate evaluation algorithm being an algorithm adapted to derive at least one result from at least two variables, wherein the at least one first characteristic value and the at least one second characteristic value are used as the at least two variables, thereby deriving at least one estimate value for at least one target variable Y of the state variables;

determining a concentration of the at least one analyte by using the at least one target variable Y.

Embodiment 2

The method according to the preceding embodiment, wherein the state variables are selected from the group consisting of: a composition of the sample of the body fluid, preferably a content of at least one component of the sample of the body fluid and more preferably a concentration of at least one analyte; a content of at least one particulate component of the sample of the body fluid, preferably a hematocrit; a temperature of the sample of the body fluid; a humidity of an ambient atmosphere surrounding the sample of the body fluid; a storage time of the test substance; an interfering substance; alterations of the sample or of certain properties of the sample caused by pharmacological treatment of a donor of the sample.

Embodiment 3

The method according to one of the preceding embodiments, wherein the first evaluation rule may not be transformed into the second evaluation rule by a time transformation.

Embodiment 4

The method according to one of the preceding embodiments, wherein the second evaluation rule differs from the first evaluation rule in at least one coefficient and/or in at least one parameter and/or in at least one component related to the algorithm.

Embodiment 5

The method according to the preceding embodiment, wherein the algorithm of the first evaluation rule differs from the algorithm of the second evaluation rule in a point in time.

Embodiment 6

The method according to one of the preceding embodiments, wherein a third evaluation rule is provided, wherein, in step c), the at least one first characteristic value is derived from the first evaluation rule, and wherein, in the multivariate evaluation algorithm, the second evaluation rule or the third evaluation rule is used depending on the at least one first characteristic value.

Embodiment 7

The method according to one of the preceding embodiments, wherein the first characteristic value is determined by using a first time interval of the optical measurement curve, wherein the second characteristic value is determined by using a second time interval of the optical measurement curve, wherein the first time interval of the optical measurement curve is different from the second time interval of the optical measurement curve.

Embodiment 8

The method according to the preceding embodiment, wherein the target value is different from the concentration of the at least one analyte.

Embodiment 9

The method according to one of the preceding embodiments, wherein the at least two evaluation rules are adapted to derive the characteristic values from at least two derivatives of the optical measurement curve.

Embodiment 10

The method according to the preceding embodiment, wherein the at least two derivatives are derivatives comprising at least two derivatives of different order.

Embodiment 11

The method according to one of the two preceding embodiments, wherein the derivatives are generated by using at least one filtering algorithm, preferably a Savitzky-Golay filtering algorithm.

Embodiment 12

The method according to one of the preceding embodiments, wherein the set of characteristic values contains 2-20 characteristic values, preferably 3-10 characteristic values.

Embodiment 13

The method according to one of the preceding embodiments, wherein the target variable Y comprises the concentration of the at least one analyte in the sample of the body fluid.

Embodiment 14

The method according to one of the preceding embodiments, wherein, in step d), in addition to the at least one target variable Y, at least one electrochemical measurement value is used for determining the concentration of the analyte, wherein the electrochemical measurement value is determined by using at least one electrochemical measurement.

Embodiment 15

The method according to the preceding embodiment, wherein, by using the electrochemical measurement value, an approximated value of the concentration of the at least one analyte in the sample of the body fluid is determined, wherein the target value Y is used for correcting the approximated value.

Embodiment 16

The method according to one of the preceding embodiments, wherein the predetermined multivariate evaluation algorithm comprises at least one polynomial algorithm selected from:

$$Y = A \cdot X, \quad (1);$$

$$Y = X^T \cdot A \cdot X, \quad (2); \text{ and}$$

$$Y = X^T \cdot (X^T \cdot A \cdot X), \quad (3),$$

wherein A is a one-dimensional, a two-dimensional or a three-dimensional evaluation tensor.

Embodiment 17

The method according to one of the preceding embodiments, wherein the predetermined multivariate evaluation algorithm comprises at least one algorithm selected from:

$$Y = \Sigma_i a_i \cdot X_i, \quad (4);$$

$$Y = \Sigma_i a_i \cdot X_i + \Sigma_{i,j} a_{ij} \cdot X_i \cdot X_j, \quad (5); \text{ and}$$

$$Y = \Sigma_i a_i \cdot X_i + \Sigma_{i,j} a_{ij} \cdot X_i \cdot X_j + \Sigma_{i,j,k} a_{ijk} \cdot X_i \cdot X_j \cdot X_k, \quad (6).$$

wherein $a_i$, $a_{ij}$, $a_{ijk}$ may be predetermined coefficients, and wherein i, j and k may be mutually independent, integers from 1 to N.

Embodiment 18

The method according to the preceding embodiment, further comprising at least one calibration step, wherein, in the calibration step, a plurality of calibration measurement curves is generated by acquiring measurement curves of a plurality of calibration fluids with the respective known target variables Y, wherein the characteristic values are determined for each calibration measurement curve, wherein an equation system comprising the coefficients of one or more of equations (4)-(6) is solved, thereby determining numeric values for the coefficients.

Embodiment 19

The method according to the preceding embodiment, wherein, in step b), the evaluation rules are adapted such that the characteristic values are linearly independent, thereby generating unique solutions for the numeric values of the coefficients.

Embodiment 20

The method according to one of the preceding embodiments, wherein the at least one multivariate evaluation algorithm comprises at least one algorithm selected from the group consisting of: a partial least squares regression algorithm (PLSR); a principal component regression algorithm (PCR); a support vector machine algorithm (SVM); an artificial neuronal network algorithm (ANN); a genetic algorithm (GA).

Embodiment 21

The method according to one of the preceding embodiments, wherein the at least one multivariate evaluation algorithm comprises a function involving at least one decision tree, wherein the decision tree comprises at least one decision branch which allows selecting one out of at least two alternative procedures based on an assessment whether a predetermined condition may be fulfilled.

Embodiment 22

The method according to the preceding embodiment, wherein the decision branch offers a decision between performing or not performing a specific procedure or performing the specific procedure under a specific parameter, with a specific parameter set, or within a specific parameter range.

Embodiment 23

The method according to the preceding embodiment, wherein the specific parameter comprises the characteristic value.

Embodiment 24

The method according to one of the preceding embodiments, wherein the body fluid is selected from the group consisting of blood, interstitial fluid, urine, plasma, serum and saliva.

Embodiment 25

The method according to one of the preceding embodiments, wherein the monitoring of the time development of the at least one measurement value indicating the progress of the detection reaction is adapted to be an impact-free monitoring of the detection reaction without influencing the detection reaction.

Embodiment 26

The method according to one of the preceding embodiments, wherein at least one of the two different evaluation rules is selected from the group consisting of:

using a specific measurement value of the optical measurement curve or a derivative of the optical measurement curve at a predetermined point in time as the characteristic value, preferably using one or more specific criteria, particularly using one or more specific conditions, which may comprise at least one end value criterion, more preferably a change rate below a predetermined threshold value;

using a mean value of the optical measurement curve or a derivative of the optical measurement curve over a predetermined period of time as the characteristic value;

using a characteristic point in time of the optical measurement curve or of a derivative of the optical measurement curve as the characteristic value, preferably a characteristic point in time at which one or more of the following occur: a maximum of the optical measurement curve or of a derivative of the optical measurement curve; a minimum of the optical measurement curve or of a derivative of the optical measurement curve; an inflection point of the optical measurement curve or of a derivative of the optical measurement curve;

using a characteristic parameter of the optical measurement curve or of a derivative of the optical measurement curve as the characteristic value, preferably a characteristic parameter at one of: a maximum of the optical measurement curve or of a derivative of the optical measurement curve; a minimum of the optical measurement curve or of a derivative of the optical measurement curve; an inflection point of the optical measurement curve or of a derivative of the optical measurement curve;

using a fit parameter derived by at least one fitting process as the characteristic value, wherein the fitting process implies a fitting of at least one predetermined fit curve to at least a section of the optical measurement curve or of a derivative of the optical measurement curve; and using at least one value derived from a phase plot of at least two derivatives of different order of the optical measurement curve as the characteristic value, wherein the phase plot comprises at least one phase space curve, wherein the value derived from the phase plot preferably is selected from the group consisting of: a position of a center of the phase space curve; a length of the phase space curve; a phase space volume; a phase space area; a point with a maximal distance to the center of the phase space curve; a mean squared distance from the origin of the phase space.

Embodiment 27

The method according to the preceding embodiment, wherein at least two different evaluation rules selected from different members of the group a.-f. are selected.

Embodiment 28

The method according to one of the preceding embodiments, wherein step b) comprises generating the set of evaluation rules, the generating of the set of evaluation rules comprising the following sub-steps:

b1) providing a learning set of learning measurement curves, acquired by using a learning set of learning body fluids and by monitoring detection reactions of a test substance and the test body fluids, wherein the test body fluids and the detection reactions are chosen such that the learning measurement curves are acquired with differing sets of state variables;

b2) identifying a set of candidate evaluation rules and deriving a set of candidate characteristic values from the learning set of learning measurement curves;

b3) determining a correlation between the candidate characteristic values for each candidate evaluation rule and the state variables;

b4) selecting the set of evaluation rules from the set of candidate evaluation rules by accounting for the correlations determined in sub-step b3).

Embodiment 29

The method according to the preceding embodiment, wherein sub-step b3) includes determining at least one correlation parameter for each candidate evaluation rule for each state variable, preferably a Pearson correlation coefficient.

Embodiment 30

The method according to one of the two preceding embodiments, wherein, in sub-step b4), a Merit value is calculated for each correlation, wherein the selecting of the set of evaluation rules from the set of candidate evaluation rules is performed by accounting for the Merit values.

Embodiment 31

The method according to one of the three preceding embodiments, wherein, in sub-step b4), a candidate evaluation rule is determined to be an evaluation rule if the corresponding correlation determined in sub-step b3) fulfils at least one predetermined condition.

Embodiment 32

A method for detecting an analyte in a body fluid sample, the method comprising the following steps:

providing at least one measurement curve, wherein the measurement curve contains a plurality of measurement values recorded by monitoring a time development of at least one measurement value indicating a progress of a detection reaction of at least one test substance and the body fluid sample, wherein the measurement values contained in the measurement curve are acquired at differing points in time, wherein the detection reaction is known to be influenced by a set of state variables, each state variable characterizing at least one of a state of the body fluid sample and a condition of the detection reaction;

determining at least one target variable and/or at least one estimate value for at least one Y by using a first time interval $t_1$ of the measurement curve, wherein $0 \leq t_1 \leq x$, wherein the target variable Y is different from at least one analyte concentration; determining at least one analyte concentration by using the at least one target variable;

providing a set of at least two different evaluation rules, each evaluation rule being adapted to derive a characteristic value from the measurement curve, thereby deriving a set of characteristic values $X=\{X_i\}_{i=1 \ldots N}$ from the measurement curve, the set of characteristic values comprising at least one first characteristic value being derived from the measurement curve by using at least one first evaluation rule from the set of evaluation rules and at least one second characteristic value being derived from the measurement curve by using at least one second evaluation rule from the set of evaluation rules, the second evaluation rule being different from the first evaluation rule.

Embodiment 33

The method according to the preceding embodiment, wherein the method further comprises the following step:

performing at least one multivariate analysis of the at least one first characteristic value and the at least one second characteristic value by using at least one predetermined multivariate evaluation algorithm, the multivariate evaluation algorithm being an algorithm adapted to derive at least one result from at least two variables, wherein the at least one first characteristic value and the at least one second characteristic value are used as the at least two variables, thereby deriving the at least one estimate value for at least one target variable Y of the state variables.

Embodiment 34

The method according to the preceding embodiment, wherein the second evaluation rule differs from the first evaluation rule in at least one coefficient and/or in at least one parameter and/or in at least one component related to the algorithm.

Embodiment 35

The method according to one of the three preceding embodiments, wherein the measurement curve is an optical measurement curve.

Embodiment 36

The method according to one of the four preceding embodiments, wherein the measurement values contained in the optical measurement curve are acquired at identical measuring conditions.

Embodiment 37

The method according to one of the five preceding embodiments, wherein the first evaluation rule may not be transformed into the second evaluation rule by a time transformation.

Embodiment 38

A method for characterizing a sample of a body fluid, the method comprising the following steps:

bringing the sample of the body fluid into contact with at least one test substance, thereby initiating a detection reaction of the test substance and the sample of the body fluid, wherein the detection reaction is known to be influenced by a set of state variables, each state variable characterizing at least one of a state of the sample of the body fluid and a condition of the detection reaction;

monitoring a time development of at least one measurement value indicating a progress of the detection reaction, thereby recording an optical measurement curve containing a plurality of the measurement values acquired at differing points in time;

evaluating the optical measurement curve by using the method according to one of the preceding embodiments.

Embodiment 39

A computer program including computer-executable instructions for performing the method according to one of the preceding embodiments when the program is executed on a computer or computer network.

Embodiment 40

An evaluation device for evaluating an optical measurement curve for analyzing at least one sample of a body fluid, the device comprising at least one evaluation unit, wherein the evaluation unit is adapted to perform a method according to one of the preceding embodiments referring to a method for evaluating a measurement.

Embodiment 41

A sample analysis device for characterizing a sample of a body fluid, the device comprising:

at least one measuring unit for measuring a detection reaction of at least one test substance and at least one sample of a body fluid, wherein the detection reaction is known to be influenced by a set of state variables, each state variable characterizing at least one of a state of the sample of the body fluid and a condition of the detection reaction, the measuring unit further being adapted for monitoring a time development of at least one measurement value indicating a progress of the detection reaction, thereby recording an optical measurement curve containing a plurality of the measurement values acquired at different points in time; and at least one evaluation device according to the preceding embodiment.

Embodiment 42

The sample analysis device according to the preceding embodiment, furthermore comprising at least one test element, preferably at least one test strip, wherein the test element contains the at least one test substance adapted to perform the detection reaction, wherein the sample analysis device is adapted such that the sample of the body fluid is applicable to the test element.

Embodiment 43

The sample analysis device according to the preceding embodiment, wherein the sample analysis device is embodied as a hand-held device.

LISTING OF REFERENCE NUMBERS 110 sample analysis device
112 measuring unit
114 evaluation device
116 evaluation unit
118 test element
120 test strip
122 hand-held device
124 monitor
126 input panel
128 light source
130 detector
132 computer
134 computer network
136 points in time
138 characteristic value
140 curve
142 curve
144 curve
146 curves
148 curves
150 curves
152 curves
154 first decision tree
156 hematocrit correction
158 predetermined hematocrit range
160 determination of the glucose concentration
162 determination of the target value
164 second decision tree
166 determination of the end value
168 predetermined glucose concentration range
170 first and second threshold values
172 first and second threshold values
174 third decision tree
176 determination of decay constant
178 further assessment
180 additional evaluation procedure

The invention claimed is:

1. A method for determining at least one analyte concentration in a body fluid sample, the method comprising the steps of:

a) obtaining, using a measuring unit, a plurality of measurement values that each indicate a progress of a detection reaction of at least one test substance and at least one body fluid sample at differing points in time, wherein the detection reaction is influenced by a set of state variables, each state variable characterizing at least one of a state of the body fluid sample and a condition of the detection reaction;

b) generating, using at least one processor, at least one optical measurement curve, wherein the optical measurement curve contains the plurality of measurement values;

c) providing, using the at least one processor, a set of at least two different evaluation rules, the at least two evaluation rules adapted to derive a characteristic value from at least two derivatives of the optical measurement curve, thereby deriving a set of characteristic values $X=\{X_i\}_{i=1\ldots N}$ from the optical measurement curve, the set of characteristic values comprising at least one first characteristic value being derived from the optical measurement curve by using at least one first evaluation rule from the set of evaluation rules and at least one second characteristic value being derived from the optical measurement curve by using at least one second evaluation rule from the set of evaluation rules, the second evaluation rule being different from the first evaluation rule;

d) performing, using the at least one processor, at least one multivariate analysis of the at least one first characteristic value and of the at least one second characteristic value by using at least one predetermined multivariate evaluation algorithm, the at least one multivariate evaluation algorithm adapted to derive at least one result from at least two variables, wherein the at least one first characteristic value and the at least one second characteristic value are used as the at least two variables, thereby deriving at least one estimate value for at least one target variable Y of the state variables; and e) determining, using the at least one processor, at least one analyte concentration by using the at least one target variable Y.

2. The method of claim 1, wherein the state variables are selected from the group consisting of a composition of the body fluid sample; a content of at least one particulate component of the body fluid sample; a temperature of the body fluid sample; a humidity of an ambient atmosphere surrounding the body fluid sample; a storage time of the test substance; an interfering substance; alterations of the body fluid sample or of certain properties of the body fluid sample caused by pharmacological treatment of a donor of the body fluid sample.

3. The method of claim 2, wherein the particulate component of the body fluid sample is a hematocrit.

4. The method of claim 1, wherein the first evaluation rule may not be transformed into the second evaluation rule by a time transformation.

5. The method of claim 1, wherein the second evaluation rule differs from the first evaluation rule in at least one of: in at least one coefficient, in at least one parameter, and in at least one component related to the at least one predetermined multivariate evaluation algorithm.

6. The method of claim 1, wherein a third evaluation rule is provided, wherein in step d), the at least one first characteristic value is derived from the first evaluation rule, and wherein in the at least one multivariate evaluation algorithm, the second evaluation rule or the third evaluation rule is used depending on the at least one first characteristic value.

7. The method of claim 1, wherein the first characteristic value is determined by using a first time interval of the optical measurement curve, wherein the second characteristic value is determined by using a second time interval of the optical measurement curve, and wherein the first time interval of the optical measurement curve is different from the second time interval of the optical measurement curve.

8. The method of claim 7, wherein the target variable Y is different from the at least one analyte concentration.

9. The method of claim 1, wherein the target variable Y comprises the at least one analyte concentration in the body fluid sample.

10. The method of claim 1, wherein in step e), in addition to the at least one target variable Y, at least one electrochemical measurement value is used for determining the at least one analyte concentration, and wherein the electrochemical measurement value is determined by using at least one electrochemical measurement.

11. The method of claim 10, wherein by using the electrochemical measurement value, an approximated value of the at least one analyte concentration in the body fluid sample is determined, and wherein the target variable Y is used for correcting the approximated value.

12. The method of claim 1, wherein the predetermined multivariate evaluation algorithm comprises at least one polynomial algorithm selected from:

$$Y = A \cdot X, \quad (1);$$

$$Y = X^T \cdot A \cdot X, \quad (2); \text{ and}$$

$$Y = X^T \cdot (X^T \cdot A \cdot X), \quad (3),$$

wherein A is a one-dimensional, a two-dimensional or a three-dimensional evaluation tensor.

13. The method of claim 1, wherein the predetermined multivariate evaluation algorithm comprises at least one algorithm selected from:

$$Y = \Sigma_i a_i \cdot X_i, \quad (4);$$

$$Y = \Sigma_i a_i \cdot X_i + \Sigma_{i,j} a_{ij} \cdot X_i \cdot X_j, \quad (5); \text{ and}$$

$$Y = \Sigma_i a_i \cdot X_i + \Sigma_{i,j} a_{ij} \cdot X_i \cdot X_j + \Sigma_{i,j,k} a_{ijk} \cdot X_i \cdot X_j \cdot X_k, \quad (6).$$

wherein $a_i$, $a_{ij}$, $a_{ijk}$ are predetermined coefficients, and wherein i, j and k are, mutually independently, integers from 1 to N.

14. The method of claim 1, wherein the at least one multivariate evaluation algorithm comprises a function involving at least one decision tree, and wherein the decision tree comprises at least one decision branch that allows selecting one out of at least two alternative procedures based on an assessment whether a predetermined condition may be fulfilled.

15. The method of claim 1, wherein at least one of the two different evaluation rules is selected from the group consisting of:
  i) using a specific measurement value of the optical measurement curve or a derivative of the optical measurement curve at a predetermined point in time as the characteristic value;
  ii) using a mean value of the optical measurement curve or a derivative of the optical measurement curve over a predetermined period of time as the characteristic value;
  iii) using a characteristic point in time of the optical measurement curve or of a derivative of the optical measurement curve as the characteristic value;
  iv) using a characteristic parameter of the optical measurement curve or of a derivative of the optical measurement curve as the characteristic value;
  v) using a fit parameter derived by at least one fitting process as the characteristic value, wherein the fitting process implies a fitting of at least one predetermined fit curve to at least a section of the optical measurement curve or of a derivative of the optical measurement curve; and
  vi) using at least one value derived from a phase plot of at least two derivatives of different order of the optical measurement curve as the characteristic value, wherein the phase plot comprises at least one phase space curve.

16. The method of claim 1, wherein step c) comprises generating the set of evaluation rules, and wherein generating of the set of evaluation rules comprising the sub-steps of:
  c1) providing a learning set of learning measurement curves, acquired by using a learning set of learning body fluids and by monitoring detection reactions of a test substance and test body fluids, wherein the test body fluids and the detection reactions are chosen such that the learning measurement curves are acquired with differing sets of state variables;
  c2) identifying a set of candidate evaluation rules and deriving a set of candidate characteristic values from the learning set of learning measurement curves;
  c3) determining a correlation between the candidate characteristic values for each candidate evaluation rule and the state variables; and
  c4) selecting the set of evaluation rules from the set of candidate evaluation rules by accounting for the correlations determined in sub-step b3).

17. A method of characterizing a body fluid sample, the method comprising the steps of:
- A) bringing the body fluid sample into contact with at least one test substance, thereby initiating a detection reaction of the test substance and the body fluid sample, wherein the detection reaction is influenced by a set of state variables, each state variable characterizing at least one of a state of the body fluid sample and a condition of the detection reaction;
- B) evaluating the optical measurement curve by using the method of claim 1.

18. A computer program comprising computer-executable instructions for performing the method of claim 1 when the program is executed on a computer or a computer network.

19. A sample analysis device for characterizing a body fluid sample, the device comprising:
- at least one measuring unit for measuring a detection reaction of at least one test substance and at least one body fluid sample, wherein the detection reaction is known to be influenced by a set of state variables, each state variable characterizing at least one of a state of the body fluid sample and a condition of the detection reaction, wherein the measuring unit is further adapted for monitoring a time development of at least one measurement value indicating a progress of the detection reaction, thereby recording an optical measurement curve containing a plurality of the measurement values acquired at different points in time; and
- at least one evaluation device for evaluating an optical measurement curve for analyzing the at least one body fluid sample, wherein the device comprises at least one evaluation unit, and wherein the evaluation unit comprises the at least one processor, and is adapted to perform the method of claim 1.

20. The sample analysis device of claim 19 further comprising at least one test element, wherein the test element comprises the at least one test substance adapted to perform the detection reaction, and wherein the sample analysis device is adapted so that the body fluid sample is applicable to the test element.

* * * * *

UNITED STATES PATENT AND TRADEMARK OFFICE
CERTIFICATE OF CORRECTION

| | |
|---|---|
| PATENT NO. | : 10,984,892 B2 |
| APPLICATION NO. | : 16/502363 |
| DATED | : April 20, 2021 |
| INVENTOR(S) | : Simon Aigner et al. |

It is certified that error appears in the above-identified patent and that said Letters Patent is hereby corrected as shown below:

In the Specification

Column 40, Line 27, "tin s" should be --t in s--.

Signed and Sealed this
Tenth Day of May, 2022

Katherine Kelly Vidal
*Director of the United States Patent and Trademark Office*